United States Patent [19]

Schreiber

[11] Patent Number: 4,672,044

[45] Date of Patent: Jun. 9, 1987

[54] MURINE MONOCLONAL ANTIBODY COMBINING SITE TO HUMAN C3B RECEPTOR (CR1)

[75] Inventor: Robert D. Schreiber, Encinitas, Calif.

[73] Assignee: Scripps Clinic & Research Foundation, La Jolla, Calif.

[21] Appl. No.: 644,217

[22] Filed: Aug. 24, 1984

[51] Int. Cl.$^4$ ............... C07K 15/04; C12N 5/00; G01N 33/577

[52] U.S. Cl. ................... 436/501; 436/504; 436/506; 436/507; 436/512; 436/518; 436/536; 436/540; 436/548; 436/815; 436/821; 435/4; 435/7; 435/68; 435/172.2; 435/240; 435/810; 935/104; 935/110

[58] Field of Search ............ 260/112.5 R; 424/85, 424/177, 1.1; 435/4, 7, 68, 70, 172.2, 240, 948, 810; 436/504, 506, 507, 512, 518, 536–542, 548, 804, 815, 821, 823, 828, 810, 501; 935/93, 104, 110, 58–85; 530/387

[56] References Cited

U.S. PATENT DOCUMENTS 4,342,566 8/1982 Theofilopoulos et al. ............ 23/230
4,361,549 11/1982 Kung et al. ............................ 424/85
4,381,292 4/1983 Bieber et al. ........................... 424/1

OTHER PUBLICATIONS

Davis, B. et al, *Microbiology*, 3rd ed., Harper & Row, Publishers, Philadelphia, (1980), pp. 361–364.
Paul, W. E. et al, *Fundamental Immunology*, Raven Press, New York, (1984), pp. 157–159.
Hogg, N. et al, *Eur. J. Immunol.*, vol. 14, pp. 236–243, (1984).
Dierich, M. P. et al, *Immunol.*, vol. 45, pp. 85–96, (1982).
Gerdes, J. et al, *Immunol.*, vol. 45, pp. 645–653, (1982).
Iida, K. et al, *J. Exper. Med.*, vol. 155, pp. 1427–1438, (1982).
Nelson, *Science*, 118, 733–737, (1953).
Fearon, *Proc. Natl. Acad. Sci. (U.S.A.)*, 76, 5867–5871, (1979).
Fearon, *J. Exp. Med.*, 152, 20–30, (1980).
Dobson et al., *J. Immunol.*, 126, 693–698, (1981).
Iida et al., *J. Immunol.*, 130, 1876–1880, (1983).
Schmitt et al., *J. Immunol.*, 126, 2042–2047, (1981).
Fearon, *Springer Semin. Immunopathol.*, 6, 159–172, (1983).
Tedder et al., *J. Immunol.*, 130, 1668–1673, (1983).
Kazatchkine et al., *J. Clin. Invest.*, 69, 900–912, (1982).
Gerdes et al., *Clin. Exp. Immunol.*, 48, 348–352, (1982).
Hoffman, *Immunochemistry*, 6, 391–403, 405–419, (1969).
Ross et al., *J. Immunol.*, 129, 2051–2060, (1982).
Pangburn et al., *Proc. Natl. Acad. Sci. (U.S.A.)*, 80, 5430–5434, (1983).
Nicholson-Weller et al., *J. Immunol.*, 129, 184–189, (1982).
Pangburn et al., *J. Exp. Med.*, 157, 1971–1980, (1983).
Aikawa et al., *J. Lab. Clin. Med.*, 94, 902–916, (1979).
Medof et al., *J. Clin. Lab. Immunol.*, 7, 7–13, (1982).
Rothman et al., *J. Immunol.*, 115, 1312–1315, (1975).
Medof et al., *J. Immunol.*, 130, 1336–1340, (1983).
Griffin et al., *J. Exp. Med.*, 142, 1263–1282, (1975).
Wilson et al., *N. Engl. J. Med.*, 307, 981–986, (1982).
Scatchard, *Ann. N.Y. Acad. Sci.*, 51, 660–672, (1949).
Fearon et al., *J. Immunol.*, 130, 370–375, (1983).
Kohler et al., *Nature*, 256, 495–497, (1975).
Shulman et al., *Nature*, 276, 269–270, (1978).

(List continued on next page.)

*Primary Examiner*—Charles F. Warren
*Assistant Examiner*—M. Moskowitz
*Attorney, Agent, or Firm*—Dressler, Goldsmith, Shore, Sutker & Milnamow, Ltd.

[57] ABSTRACT

A murine monoclonal antibody combining site produced by a hybridoma formed by fusion of cells from a myeloma cell line and lymphocytes that produce antibodies that react (1) with isolated human C3b receptor and (2) with C3b receptor-bearing cells from a mammal immunized with human C3b receptor is disclosed.

16 Claims, 7 Drawing Figures

OTHER PUBLICATIONS

Galfre et al., *Nature*, 277, 131–133, (1979).
Goding, "Production of Monoclonal Antibodies by Cell Fusion" in *Antibody as a Tool*, Marchalonis et al., eds. John Wiley & Sons, Ltd., p. 273, (1982), to p. 289.
Stryer, *Biochemistry*, 2d ed., W. H. Freeman & Co., San Francisco, p. 16, (1981).
Medof et al., *J. Exp. Med.*, 156, 1739–1754, (1982).
Miyakawa et al., *Lancet*, 2, 493–497, (1981).
Buffone et al., *Clin. Chem.*, 29, 1720–1723, (1983).
Moran et al., *Lancet*, 2, 572–573, (1972).
Chakrabarty, et al., *Clin. Exp. Immunol.*, 51, 225–231, (1983).
Yancey et al., *J. Am. Acad. Dermatol.*, 10, 711–731, (1984).
Inada et al., *Clin. Exp. Immunol.*, 50, 189–197, (1982).
Medof et al., *Proc. Natl. Acad. Sci. (U.S.A.)*, 79, 5047–5051, (1982).
DeLuca, "Immunofluorescence Analysis" in *Antibody as a Tool*, Marchalonis et al., eds. John Wiley & Sons, Ltd., pp. 189–231, (1982).
Pykett, *Scientific American*, 246, 78–88, (1982).
Hammer et al., *J. Biol. Chem.*, 256, 3995–4003, (1981).
Ballow et al., *J. Immunol.*, 103, 944–952, (1969).
Schreiber et al., *J. Exp. Med.*, 142, 760–772, (1975).
Gotze et al., *J. Exp. Med.*, 134, 905–108, (1971).
Lesavre et al., *J. Immunol.*, 123, 529–534, (1979).

MURINE MONOCLONAL ANTIBODY COMBINING SITE TO HUMAN C3B RECEPTOR (CR1)

The Government of the United States of America has certain rights in this invention pursuant to Grant No. AI 17354 awarded by the United States Public Health Service.

DESCRIPTION

1. Technical Field of the Invention

The present invention relates to murine monoclonal antibody combining sites, and more particularly, to molecules that contan murine monclonal antibody combining sites that react with human C3b receptor and with C3b receptor-bearing cells.

2. Background of the Invention

The complement system is a complex group of proteins present in body fluids that, working together with antibodies or other factors, plays an important role as mediators of immune, allergic, immunochemical and immunopathological reactions. Activation of the complement system can result in a wide range of reactions such as lysis of various kinds of cells, bacteria and protozoa, inactivation of viruses, and the direct mediation of inflammatory processes. Through the hormone-like activity of several of its components, the complement system can recruit and enlist the participation of other humoral and cellular effector systems. These in turn can induce directed migration of leukocytes, trigger histamine release from mast cells, and stimulate the release of lysosomal constituents from phagocytes.

The complement system consists of at least twenty distinct plasma proteins capable of interacting with each other, with antibodies, and with cell membranes. Many of these proteins, when activated, combine with some of the other proteins to form enzymes that cleave and activate still other proteins in the system. The sequential activation of these proteins follows two main pathways, the classical pathway and the alternative pathway. Both pathways use a common terminal trunk that leads to cell lysis or virus inactivation.

The classical pathway can be activated by antigen-antibody complexes, aggregated immunoglobulins and non-immunological substances such as DNA and trypsin-like enzymes. The classical pathway of activation involves, successively, four components denominated C1, C4, C2 and C3. These components can be grouped into two functional units: C1 or recognition unit; and C4, C2, and C3 or activation unit. Five additional components denominated C5, C6, C7, C8, and C9 define the membrane attack unit forming the terminal trunk common to both pathways.

The alternative pathway, also known as the properdin pathway, comprises at least six components. Five of these components truly belong to the alternative pathway: factors B, D, properdin (P), and two inhibitors, H and I. The sixth component, C3, is also be found in the classical pathway. Component C3b is sometimes also known as factor A. The alternative pathway can be activated by immunological substances such as IgA and non-immunological substances such as certain complex polysaccharides, trypsin-like enzymes and cobra venom factor. Even in the absence of any antibody or immunoglobulin, the alternative pathway can destroy microorganisms.

When either pathway of the complement system is activated, component C3 is proteolytically cleaved into components C3a and C3b. C3b, through an ester bond, can link to biological membranes or particles. C3b also cooperates with other components in the complement system such as factor B and properdin, or C4b and C2a to activate the membrane attack complex of components C5 though C9.

C3b can be proteolytically cleaved by factors H and I together, or by factor I alone where the C3b is bound to a type 1 complement receptor (CR1), to generate the inactivated molecule iC3b. The iC3b molecule can then go through several degradations to form C3d, C3c and C3d,g, also known as alpha-2D. C3d,g can be cleaved to form C3d and C3g with the ester bond discussed above being on the C3d molecule. In the case of cell-bound iC3b, the degradation products C3d,g and C3d remain bound to the cell by this ester bond.

Immune complexes (ICs), composed of antigens and their respective antibodies, appear to be involved in the pathogenesis of a diverse array of human and animal diseases. These include autoimmune, infectious (bacterial, parasitic, viral), neoplastic and other unclassified disorders. The primary means by which immune complexes mediate tissue injury is activation of the complement (C) system, resulting in release of biologically active peptides (C3a, C3d,g, C5a). Along with immune complex-fixed C3 fragments, these peptides induce such biologic phenomena as immune adherence, leukocytosis, chemotaxis and release of injurious mediators and of proteolytic enzymes.

Immune complexes and C3-C5 fragments also appear to exert profound effects on a variety of immune functions, both humoral and cellular. These effects may enhance or suppress immunity, depending primarily on the antigen to antibody ratio, the isotype of antibody involved, and the balance between C3 and C5 fragments. Therefore, there is a great interest in developing techniques for detection and quantitation of immune complexes and products of activated C components.

As detailed above, activation of the complement system gives rise to a number of molecular species that can interact with host-derived cells and regulate their function. This interaction is mediated through distinct cell surface complement receptors, and receptor engagement produces biological responses that can either modulate host defense reactions or enhance inflammation.

Although the first complement receptor was recognized more than thirty years ago, Nelson, *Science*, 118, 733 (1953), detailed biochemical information concerning the receptors has only recently become available. Currently, eight distinct complement receptors are recognized. Five receptors (CR1, CR2, CR3, C3a and C3e receptors) react with various regions on C3 while the other receptors display specificity for either C1q, C5a or factor H.

The immune adherence receptor or C3b receptor, also known as CR1, was the first complement receptor to be recognized. In 1953, Nelson, supra, showed that antibody-coated microorganisms treated with complement acquired the ability to bind to human erythrocytes, a phenomenon termed "immune-adherence". Today, the C3b receptor, CR1, is the best characterized complement receptor with respect to both its chemistry and biology.

CR1 was first purified by Fearon in 1979 from detergent-solubilized human erythrocyte membranes, Fearon, *Proc. Natl. Acad. Sci. (USA)*, 76, 5867 (1979) and Fearon, *J. Exp. Med.*, 152, 20 (1980). Upon analysis by SDS polyacrylamide gel electrophoresis, the receptor was characterized as a single-chain glycoprotein with an apparent molecular weight of about 205,000 daltons. More recent molecular weight determinations indicate that the receptor displays a higher molecular weight of approximately 250,000 daltons.

Two pieces of evidence indicated that this same protein functioned as the C3b receptor of other hematopoeitic cells: (1) a polyvalent antiserum raised to the purified erythrocyte-derived CR1 inhibited rosetting of C3b-bearing erythrocytes to other C3b receptor-bearing cells; and, (2) anti-CR1 immunoprecipitated the same 205,000 molecular weight glycoprotein from radiolabeled, solubilized membranes of human erythrocytes, polymorphonuclear leukocytes, B lymphocytes and monocytes, Fearon, *J. Exp. Med., supra*, and Dobson, et al., *J. Immunol.*, 126, 693 (1981).

CR1 has been identified on a variety of somatic cells. These include erythrocytes, PMN, monocytes, B cells, Dobson et al., *J. Immunol., supra*; Fearon et al., *J. Exp. Med., supra*; Iida et al., *J. Immunol.*, 130, 1876 (1983); and Schmitt et al., *J. Immunol.*, 126, 2042 (1981); a subpopulation of T cells, Fearon, *Springer Semin. Immunopathol.*, 6, 159 (1983); and Tedder et al., *J. Immunol.*, 130, 1668 (1983); glomerular podocytes, Kazatchkine et al., *J. Clin. Invest.*, 69, 900 (1982); and dendritic reticular cells in germinal centers, Gerdes et al., *Clin Exp. Immunol.*, 48, 348 (1982).

CR1 represents the most versatile of the complement receptors because it performs the largest number of functions. It regulates complement activation at the host cell surface, functions in the processing of immune complexes and participates in a variety of host-cell mediated defense reactions. The first two functions mentioned above are unique to CR1 and may thus constitute its major biological role.

The ability of CR1 to inhibit the complement-derived C3/C5 convertases was the functional property that eventuated its purification. In 1969, an activity in butanol extracts of human erythrocyte membranes was described that inhibited erythrocyte lysis by antibody and complement, Hoffman, *Immunochemistry*, 6, 391 (1969). In its unpurified state, the factors(s) accelerated the rate of decay/dissociation of the classical pathway C3/C5 convertase, Hoffman, *Immunochemistry*, 6, 405 (1969). Ten years later, Fearon identified a similar activity from detergent-solubilized erythrocytes that inhibited the alternative pathway enzymes, Fearon, *Proc. Natl. Acad. Sci. (USA), supra*. Purification of the inhibitory protein led to its subsequent identification as the C3b receptor.

In purified form, CR1 inhibited complement activation by binding to C3b or C4b and (1) increased the rate of decay/dissociation of the alternative C3 convertase, Fearon, *Proc. Natl. Acad. Sci. (USA), supra*; and, Iida et al., *J. Immunol.*, 130, 1876 (1983), and the classical C3 convertase, Iida et al., *J. Immunol., supra*, or (2) acted as the cofactor for the factor I-dependent, cleavage of C3b to C3d,g, Fearon, *Proc. Natl. Acad. Sci. (USA), supra*; and Ross et al., *J. Immunol.*, 129, 2051 (1982), and C3c and of C4b to C4d and C4c, Iida et al., *J. Immunol., supra*.

CR1 thus resembles its serum analogs factor H and C4 binding protein (C4bp) with two important exceptions. Its specificity is more general since it reacts with either C3b or C4b and it binds to C3bi with sufficient affinity to act as the cofactor for the factor I-dependent cleavage of the molecule into C3c and C3d,g.

Cell-associated CR1 was also capable of inhibiting complement activation either on foreign particles, Iida et al., *J. Immunol., supra*, or on the receptor-bearing cell itself. CR1 appeared to be the only membrane component that could function as a factor I cofactor since the cell-derived activity was neutralized by treatment of normal cells with CR1-specific antibodies or proteases. An individual has also been identified whose erythrocytes are concomitantly devoid of both CR1 and cofactor activity, Pangburn et al., *Proc. Natl. Acad. Sci. (USA)*, 80, 5430 (1983).

However, CR1 does not appear to possess the only decay-accelerating activity present in human cell membranes. Another molecule termed decay-accelerating factor (DAF) has been purified from erythrocyte membranes, Nicholson-Weller et al., *J. Immunol.*, 129, 184 (1982), and, Pangburn et al., *Proc. Natl. Acad. Sci. (USA), supra*, that can inhibit C3/C5 convertase activity. Using blocking antisera specific for the two proteins, DAF and not CR1 appears to foster major decay-accelerating activity on the intact erythrocyte membrane, Pangburn et al., *Proc. Natl. Acad. Sci. (USA), supra*, and Pangburn et al., *J. Exp. Med.*, 157, 1971 (1983). Thus, the cofactor activity of CR1 may be its major complement regulating function.

A substantial amount of evidence also exists that suggests that CR1 plays a role in the processing of immune complexes. It has been shown that the whole blood and soluble immune complexes are opsonized by complement and bind to red blood cells through CR1, Aikawa et al., *J. Lab. Clin. Med.*, 94, 902 (1979); Cornacoff et al., *J. Clin. Invest.*, 71, 236 (1983); Medof et al., *J. Clin. Lab. Immunol.*, 7, 7 (1982); and Rothman et al., *J. Immunol.*, 115, 1312 (1975). Cornacoff et al., supra demonstrated that immune complexes are transported to the liver on erythrocyte vehicles where they dissociate from the erythrocyte and remain. The mechanism of dissociation is not yet known but may be a reflection of CR1 cofactor activity. The in vitro work of Medof et al., supra has shown that C3b-coated immune complexes bound to CR1 on erythrocytes are released upon exposure to factor I that converts the C3b to C3d,g, Medof et al., *J. Exp. Med., supra*; and, Medof et al., *J. Immunol.*, 130, 1336 (1983).

CR1 appears to direct the trafficking of immune complexes to defined organs where processing ultimately occurs. Since there is an indication that erythrocytes from all species carry CR1, this process may be of general biological importance. The observation that certain human immune complex diseases are associated with genetically reduced levels of erythrocyte CR1 provides clinical evidence to support this concept.

CR1 function is also influenced by the activation state of the receptor bearing cell. The best example of this, is phagocytosis of C3b-coated erythrocytes by macrophages. In their basal activation state, macrophages ingest EC3b only when antibody to the target cell is present. However, upon activation, ingestion can occur without the participation of immunoglobulin, Griffin et al., *J. Exp. Med.*, 142, 1263 (1975).

Studies have indicated that the level of CR1 on erythrocytes is under genetic regulation, Fearon, *N. Engl. J. Med.*, 307, 981 (1982). A correlation has also been found between low CR1 density on erythrocytes and the development of certain autoimmune diseases such as systemic lupus erythematosis, Fearon, supra.

It is thus seen that CR1 plays an important role in mammalian biology. It is also therefore seen that a means for quantitating the number of such receptors on mammalian cells could be a valuable asset for the clinician.

SUMMRY OF THE INVENTION

The present invention contemplates a molecule that contains a murine monoclonal antibody combining site-containing molecule and a method of preparing and using same as well as diagnostics utilizing the antibody combining site. The monoclonal antibody combining site is produced by a hybridoma formed by fusion of a myeloma cell line with lymphocytes that produce antibodies that react (1) with isolated human C3b receptor, and (2) with C3b receptor-bearing cells. Exemplary of lymphocytes useful for that fusion are splenocytes from a mouse immunized with human C3b receptor. The monoclonal antibody combining site-containing molecule of this invention reacts with the isolated human C3b receptor and C3b receptor bearing cells.

In one aspect of the invention, a murine monoclonal antibody containing a combining site is produced by hybridoma ATCC HB 8592. This monoclonal antibody combining site-containing molecule designated Mab 543, was formed by fusion of cells from mouse myeloma line P3X63-Ag8.653 and murine splenic cells from a mouse previously immunized with human C3b receptor. Monoclonal antibody combining site-containing molecul Mab 543 (1) reacts with human C3b receptor and with C3b receptor bearing cells; (2) when containing an Fc portion binds to *Staphyloccoccus aureus* Cowan strain (Staphylococcal protein A); (3) reacts with C3b receptors on human blood cells such as erythrocytes, polymorphonuclear leukocytes, monocytes and B lymphocytes; (4) reacts with C3b receptors on human tissue cells such as dendritic reticulum and B cells in germinal centers; and (5) has an epitopic specificity distinct from C3b ligand binding sites of the C3b receptors, and binds to C3b receptors that are occupied and are unoccupied by the C3b ligands.

In another aspect of the present invention, a diagnostic system for assaying for the presence of cellular C3b receptors and C3b receptor-bearing cells is contemplated. The system includes, in at least one container, as an active ingredient, an effective amount of the above-described mammalian monoclonal antibody combining site-containing molecule, such as the specifically described murine monoclonal antibody combining site-containing molecule class IgG. The system may also contain an indicating means.

In a further aspect of the present invention, hybridoma ATCC HB 8592 for the production of the above described murine monoclonal antibody combining site of this invention, is contemplated. The hybridoma is formed by fusion of cells from a mouse myeloma line and murine splenic cells from a mouse previously immunized with human C3b receptor.

In yet another aspect of the present invention, a method of preparing a hybridoma that produces the above described monoclonal antibody combining site is contemplated. The method comprises (a) immunizing a mammal such as a mouse with purified human C3b receptor; (b) removing the spleen from the mammal and making a suspension of the spleen cells with myeloma cells such as mouse myeloma cells in the presence of a cell fusion promoter; (d) diluting and culturing the fused cells in media that will not support the unfused myeloma cells to provide media having hybridoma cells and a supernatant; (e) evaluating the supernatants for the presence of antibody combining site-containing molecule to human C3b receptor; and (f) selecting and cloning the desired hybridoma that produces a monoclonal antibody combining site-containing molecule to human C3b receptor.

In a still further aspect of the present invention, a method of preparing the above-described murine monoclonal antibody combining site-containing molecule is contemplated. The method comprises culturing the hybridoma ATCC HB 8592 in a suitable medium and recovering the antibody combining site-containing molecule from the medium containing the hybridoma.

In yet another aspect of the present invention, a further method of preparing the above described murine monoclonal antibody combining site-containing molecule is contemplated. The method comprises injecting into a mouse the hybridoma ATCC HB 8592 and recovering the antibody combining site-containing molecule from the malignant ascites or serum of the mammal.

In a still further aspect of the present invention, a solid phase assay method for detecting the presence of cellular C3b receptors and C3b receptor-bearing cells in a sample to be assayed is contemplated. The assay method utilizes the above described monoclonal antibody combining site. The assay method may also be utilized to detect the presence of C3b receptors on erythrocytes and other blood cells of normal individuals or patients with Hansen's disease (leprosy) and other pathological disorders.

The present invention provides several benefits and advantages.

One benefit of the present invention is that the monoclonal antibody combining site-containing molecule of the present invention is useful, inter alia, for enumerating the number of C3b receptors on various cells. Another benefit is that the monoclonal antibody combining site-containing molecule of the present invention is useful in identifying individuals with low levels of C3b receptor who may therefore be at risk with respect to autoimmune diseases.

One of the advantages of the present invention is that the monoclonal antibody combining site-containing molecule of the present invention, when used to identify the presence of C3b receptors, provides more efficient and conclusive identification than the rosette analysis which has previously been so used.

Still further benefits and advantages will be apparent to those skilled in the art from the Detailed Description that follows.

BRIEF DESCRIPTION OF THE DRAWINGS

In drawings forming a portion of the disclosure of this invention.

DETAILED DESCRIPTION OF THE INVENTION

Figure 1:
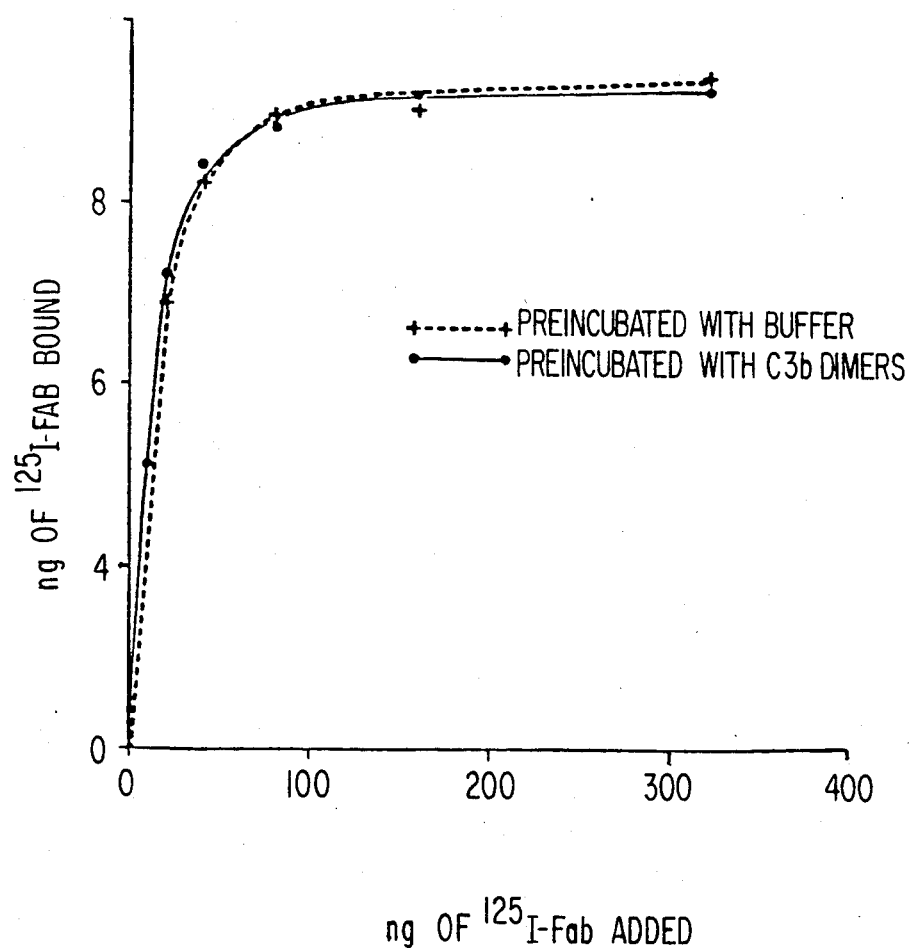
FIG. 1 is a graph illustrating the effect of cell bound C3b dimers on erythrocyte CR1 quantitation. The binding curves represent erythrocytes that were suspended in half physiological ionic strength veronal-buffered saline solution, dextrose and 0.1 percent gelatin (DGVB) at pH 7.3 (+) or C3b dimers (−) prior to CR1 quantitation with $^{125}$I-labelled Fab' portion of Mab 543.

The present invention is directed to a monoclonal antibody combining site-containing molecule and to methods of preparing and using same, as well as diagnostics utilizing the antibody combining site. The monoclonal antibody combining site-containing molecule reacts with human C3b receptor and with C3b receptor bearing cells.

I. General Discussion

The term "antibody combining site" as used herein is meant to indicate a biologically active molecule that binds to a ligand by an antibody hypervariable region. Molecules that contain antibody combining sites of the present invention are whole antibodies, substantially intact antibodies or idiotype-containing polypeptide portions of antibodies. Biological activity of an antibody combining site-containing molecule is evidenced by the binding of the site to its antigenic ligand upon their admixture in an aqueous medium, at least at physiological pH values and ionic strengths. Preferably, the site-containing molecules also bind to the antigenic ligand within a pH value range of about 5 to about 9, and at ionic strengths such as that of distilled water to that of about one molar sodium chloride.

Idiotype-containing polypeptide portions of antibodies are those portions of antibody molecules that include the idiotype and bind to the ligand, and include the Fab, F(ab')$_2$ and Fab' portions of the antibodies. Fab, F(ab')$_2$ and Fab' portions of antibodies are well known in the art, and are prepared by the reaction of papain, pepsin and pepsin followed by reduction and alkylation as discussed hereinafter, respectively, on whole or substantially intact antibodies by methods that are well known. See for example, U.S. Pat. No. 4,342,566 to Theofilopolous and Dixon.

The molecules containing antibody combining sites useful in the present invention are monoclonal antibodies. A "monoclonal antibody" (Mab) is an antibody produced by clones of a single cell called a hybridoma that secretes but one kind of antibody molecule. The hybridoma cell is produced by fusion of an antibody-producing cell and a myeloma or other self-perpetuating cell line. Such antibodies were first described by Kohler and Milstein, *Nature*, 256, 495-497 (1975), which description is incorporated herein by reference. Monoclonal antibodies are typically obtained from supernatants of hybridoma tissue cultures, the preferred method for obtaining the monoclonal antibody combining sites of the present invention, or, alternatively, from ascites fluid obtained from animals into which the hybridoma tissue was introduced. Both methods are described in detail hereinafter.

To form the hybridoma from which the monoclonal antibody is produced, a myeloma cell line is fused with mammalian lymphocytes that produce antibodies that react with isolated human C3b receptor, such as splenocytes from an animal immunized with human C3b receptor. It is preferred that the myeloma cell line be from the same species as the lymphocytes. Therefore, fused hybrids such as mouse-mouse hybrids [Shulman et al., *Nature*, 276, 269 (1978)] or rat-rat hybrids [Galfre et al., *Nature*, 277, 131 (1979)] are typically utilized. However, some rat-mouse hybrids have also been successfully used in forming hybridomas [Goding, "Production of Monoclonal Antibodies by Cell Fusion," in *Antibody as a Tool*, Marchalonis et al. eds., John Wiley & Sons Ltd., p. 273 (1982)]. Suitable myeloma lines for use in the present invention include MPC-11 (ATCC CRL 167), P3×63-Ag8.653 (ATCC CRL 1580), Sp2/O-Ag 14 (ATCC CRL 1581), P3×63 Ag8U.1 (ATCC CRL 1597), Y3-Ag1.2.3. (deposited at Collection Nationale de Cultures de Microorganisms, Paris, France, number I-078) and P3×63Ag8 (ATCC TIB 9). Myeloma line P3×63-Ag8.653 is preferred for use in the present invention.

A particular hybridoma used in producing a monoclonal antibody of the present invention was deposited on July 31, 1984 in the American Type Culture Collection of Rockville, MD and bears the designation ATCC HB 8592.

The full names for individual amino acid residues are sometimes used herein as are the well-known three-letter abbreviations. The Table of Correspondence, below, provides the full name as well as the abbreviations and symbols for each amino acid residue named herein (See, for example, L. Stryer, *Biochemistry*, 2nd ed., W. H. Freeman and Company, San Francisco, (1981), page 16.).

| Table of Correspondence | | |
|---|---|---|
| Amino acid | Three-letter abbreviation | One-letter symbol |
| Alanine | Ala | A |
| Arginine | Arg | R |
| Asparagine | Asn | N |
| Aspartic acid | Asp | D |
| Asparagine or aspartic acid | Asx | B |
| Cysteine | Cys | C |
| Glutamine | Gln | Q |
| Glutamic acid | Glu | E |
| Glutamine or glutamic acid | Glx | Z |
| Glycine | Gly | G |
| Histidine | His | H |
| Isoleucine | Ile | I |
| Leucine | Leu | L |
| Lysine | Lys | K |
| Methionine | Met | M |
| Phenylalanine | Phe | F |
| Proline | Pro | P |
| Serine | Ser | S |
| Threonine | Thr | T |
| Tryptophan | Trp | W |
| Tyrosine | Tyr | Y |
| Valine | Val | V |

The amino acid residues present in the intact Mab 543 and in its Fab' portion as determined by standard hydrolytic techniques are shown below in Table I with an accuracy believed to be ±10–20 percent:

TABLE I

| | AMINO ACID ANALYSIS | | | |
|---|---|---|---|---|
| | Residues/Molecule | | | |
| | Mab 543 (Whole) | | Mab 543 (Fab' portion) | |
| Amino Acid | Found | Rounded | Found | Rounded |
| Asx | 121.9 | 122 | 78.0 | 78 |
| Thr | 115.4 | 115 | 77.3 | 77 |
| Ser | 146.0 | 146 | 113.2 | 113 |
| Glx | 129.7 | 130 | 78.6 | 79 |
| Pro | 91.2 | 91 | 53.9 | 54 |
| Gly | 70.9 | 71 | 60.5 | 60 |
| Ala | 71.9 | 72 | 66.1 | 66 |
| Cys | 31.2 | 31 | | 71 |
| Val | 103.0 | 103 | | 7 |
| Met | 19.7 | 20 | | 29 |
| Ile | 48.8 | 49 | | 59 |
| Leu | 83.4 | 83 | | 48 |
| Tyr | 58.5 | 58 | | 32 |
| Phe | 56.2 | 56 | | 19 |
| His | 31.8 | 32 | | 45 |
| Lys | 83.3 | 83 | | 32 |
| Arg | 42.2 | 42 | | |

The murine monoclonal antibody combining site of the present invention is most preferably murine monoclonal antibody Mab 543 of class IgG that displays a kappa light chain and a gamma$_1$ heavy chain. This preferred antibody combining site-containing molecule reacts with cells bearing human C3b receptor as do all other antibody combining sites of this invention. These cells include erythrocytes, polymorphonuclear leukocytes, monocytes and B lymphocytes and tissue cells such as dendritic reticulum and B cells in germinal centers. Mab 543 also, when it contains an Fc portion, binds to *Staphylococcus aureus* protein A (Cowan strain) and has an epitope specificity distinct from the ligand binding site of C3b receptor thereby permitting detection of both occupied and unoccupied receptors.

Pepsin digestion of Mab 543 followed by reduction and alkylation with iodoacetamide produces Fab' fragments that bind to C3b receptor bearing cells with sufficient affinity to allow enumeration of receptors of various cell types. Recent studies, e.g., Medof et al., *J. Exp. Med.*, 156, 1739 (1982) have indicated that erythrocytes play an important role in the processing of immune complexes by binding C3b-coated complexes through a C3b receptor. Other studies, Fearon, *N. Engl. J. Med.*, 307, 981 (1982), have indicated that the level of C3b receptor on erythrocytes is under genetic regulation, and a correlation has been found between low C3b receptor density on erythrocytes and the development of certain autoimmune diseases such as systemic lupus erythematosis. Therefore, Mab 543 is useful in clinical analyses to identify individuals with low levels of C3b receptor who may, therefore, be at risk with respect to autoimmune disease.

A number of investigators have reported studies showing that patients with systemic lupus erythematous (SLE) and rheumatoid arthritis had reduced levels of CR1 on the surface of erythrocytes, Miyakawa et al., *Lancet*, 2, 498 (1981); Iida et al., *J. Exp. Med.*, 155, 1427, (1982); Wilson et al., *N. Engl. J. Med.*, 307, 981 (1982); Buffone et al., *Clin. Chem.*, 29, 1720 (1983). Controversy exists as to the nature of these findings. A correlation between depressed levels of CR1 and increased levels of circulating immune complexes (CIC) by Clq binding has been found in one study, Iida et al., *J. Exp. Med., supra*. This was not corroborated by reports from other investigators, Miyakawa et al., *Lancet, supra*; Wilson et al., *N. Engl. J. Med., supra*. However, none of these studies compared CR1 in SLE patients to patients with Discoid lupus erythematosus (DLE) in whom no CIC are found.

The results discussed below demonstrate the quantitation of CR1 density on the surface of erythrocytes of a normal control population and patients with Hansen's disease. This patient population was screened in order to compare the spectrum that spans from lepromatous leprosy, shown to present high levels of CIC, to the tuberculoid pole, that features, the absence of CIC, Moran et al., *Lancet*, 2, 572 (1982); Chakrabarty et al., *Clin. Exp. Immunol.*, 51, 225 (1983); Yancey et al., *J. Am. Acad. Dermatol.*, 10, 711 (1984). CR1 on human erythrocytes has been shown to accelerate the decay of the C3 convertase and act as a cofactor in the cleavage of C3b fragments. CR1 also binds to CIC that carry C3b particles, Inada et al., *Clin. Exp. Immunol.*, 50, 189 1982; Medof et al., *Proc. Natl. Acad. Sci. (USA)*, 79, 5074 (1982); Medof et al., *J. Exp. Med.*, 156, 1739 (1982), and delivers them to the liver, where they are presumably cleared by local macrophages, Cornacoff et al., *J. Clin. Invest.*, 71, 236 (1983). The high relative concentration of erythrocytes in the blood stream assigns them the major role in the binding of circulating C3b bearing particles, in spite of having less CR1 on their surface than leukocytes, Medof et al., *J. Clin. Lab. Immunol.*, 7, 7 (1982).

In addition to demonstrating the binding of Mab 543 to erythrocytes, the results discussed below also demonstrate that Mab 543 binds to other cells and tissues bearing C3b receptor, such as polymorphonuclear leukocytes and monocytes, and has an epitope specificity distinct from the ligand binding site of C3b receptor.

The results discussed below were obtained using the Mab 543 embodiment of this invention. It is to be understood, however, that the results discussed hereinbelow are illustrative of embodiments utilizing Mab 543 and the present invention is not intended to be so limited.

II. Results

A. Binding of Mab 543 to C3b Receptor Bearing Cells

The ability of Mab 543 to bind to various C3b receptor-(CR1) bearing cells and tissues was screened. In order to measure CR1 on erythrocyte surfaces, an assay using $^{125}$I-labelled Fab' portions of the IgG fraction of Mab 543 was utilized in a radiobinding assay.

Duplicate samples of 50 microliters of erythrocytes at a concentration of $2.6 \times 10^9$ per milliliter (ml) in DGVB were incubated either, with 50 microliters of DGVB or 50 microliters of C3b dimers diluted in the same buffer to a concentration of 100 micrograms/milliliter. After 45 minutes on ice, 50 microliters of dilutions of $^{125}$I-labelled Fab' portions of Mab 543 ranging from 0.1 to 6.5 micrograms/milliliter in DGVB were added to the mixtures and further incubated on ice for 45 minutes. Aliquots of 125 microliters of each sample were then layered on to 200 microliters of dibutylphthalate (Eastman Kodak, Rochester, NY) in 400 microliter polypropylene tubes (BioRad, Richmond, CA), and were centrifuged for one minute at 8000 $\times$g in a microfuge (Beckman, Palo Alto, CA). The tubes were then cut and the pellets and supernatants measured for bound and free antibody. The number of CR1 per cell was calculated by Scatchard analysis, as described by Scatchard, *Ann. N.Y. Acad. Sci.*, supra., of the binding data, as shown in FIG. 1.

Figure 2:
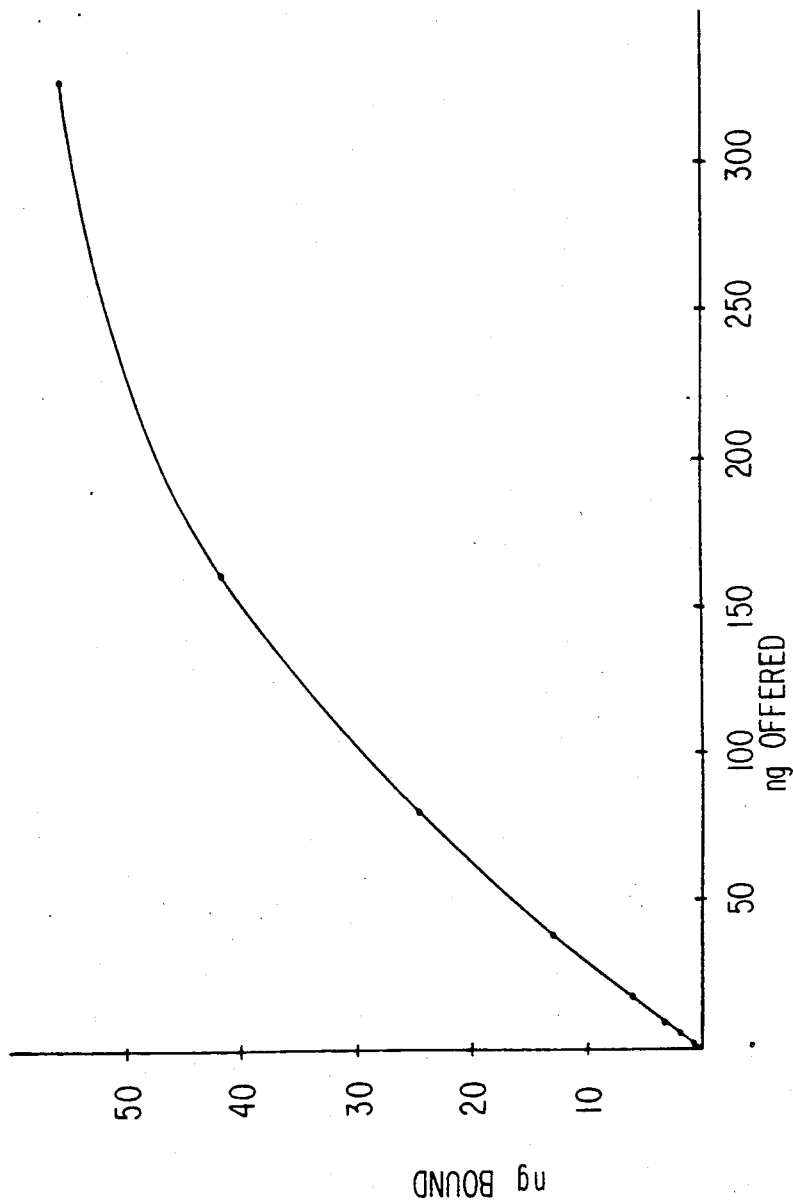
FIG. 2 is a graph illustrating the specific binding of $^{125}$I-labelled Fab' portion of Mab 543 of the present invention to CR1 on the surface of monocytes. The binding curves represent $1.25 \times 10^8$ monocytes/ml that were incubated with Hank's Balanced Salt Solution (HBSS) diluted 1:2 in water and containing 1 milligram (mg)/ml bovine serum albumin, 0.5 percent dextrose and 0.01M ethylenediaminetetraacetic acid (EDTA) [DAHBSE] prior to CR1 quantitation with $^{125}$I-labelled Fab' portion of Mab 543.

Utilizing the above assay method with varying amounts of buffer and cell concentrations in buffer, further screenings of the binding of Mab 543 to CR1 in CR1 bearing cells were made. FIG. 2 shows the results for $1.25 \times 10^8$ monocytes/ml in DAHBSE buffer.

Figure 3:
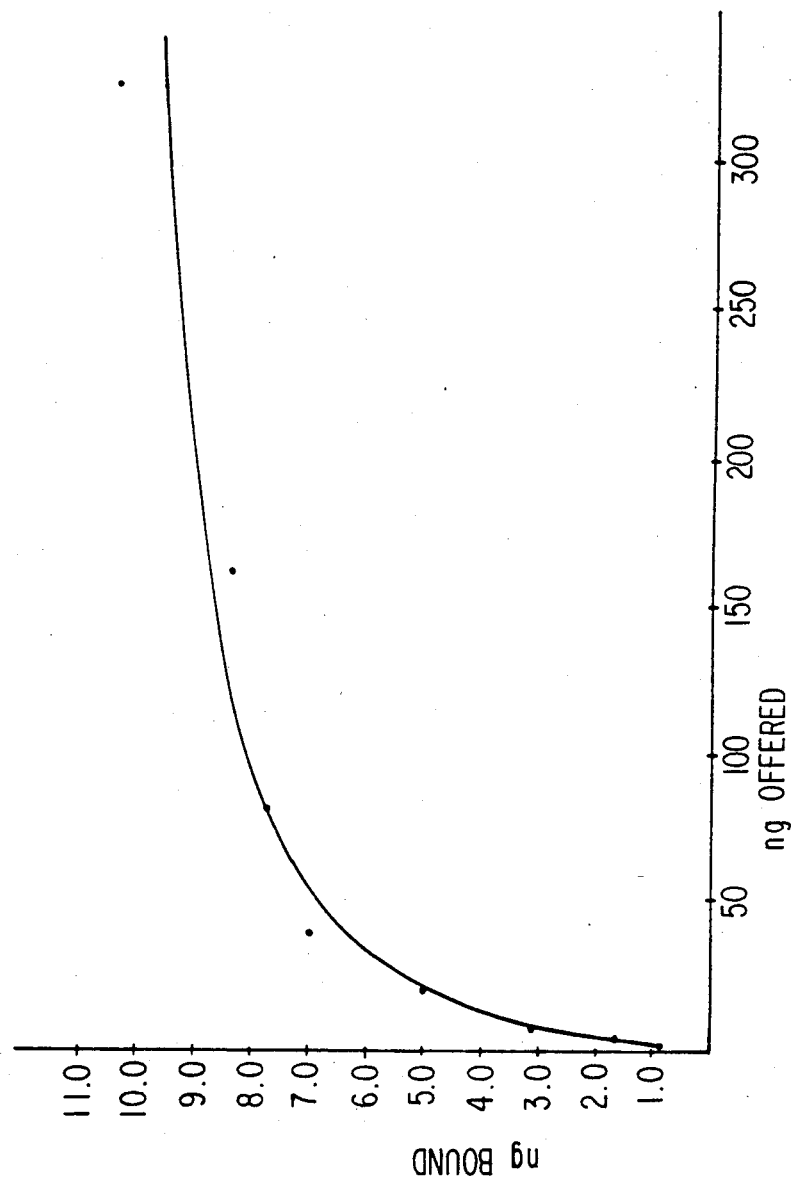
FIG. 3 is a graph illustrating the specific binding of $^{125}$I-labelled Fab' portion of Mab 543 to CR1 on the surface of human erythrocytes. The binding curves represent $2.4 \times 10^9$ erythrocytes/ml that were incubated with DGVB prior to CR1 quantitation with $^{125}$I-labelled Fab' portion of Mab 543.
Figure 4:
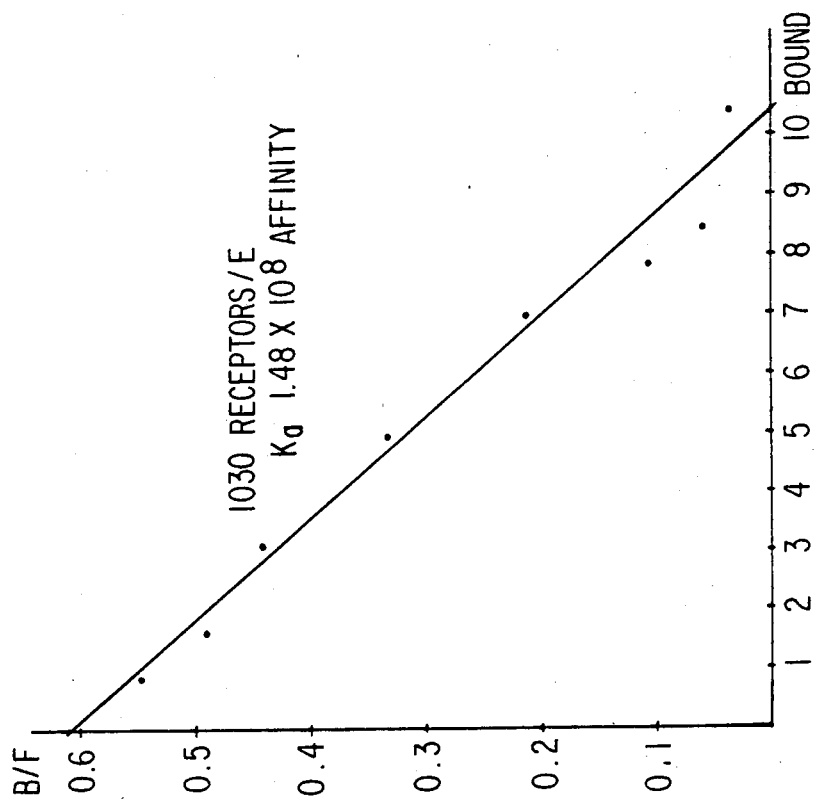
FIG. 4 is a Scatchard plot of the specific binding data of FIG. 3 to provide the total number of C3b receptors per erythrocyte plotted according to Scatchard, *Ann.-N.Y.Acad.Sci.*, 51, 660 (1949). The ordinate shows the number of Fab' molecules bound/number of free Fab' molecules and the abscissa shows the number of Fab' molecules/cell. The total number of C3b receptors per cell is 1030 as indicated by the point on the abscissa where the plot intersects it.

FIGS. 3 and 4 show further results for screenings with human erythrocytes. The binding data in FIGS. 3 and 4 indicates that about 1030 CR1/cell were found with an affinity, ($K_a$) of the ligand for the receptor of $1.48 \times 10^8$ M$^{-1}$.

Figure 5:
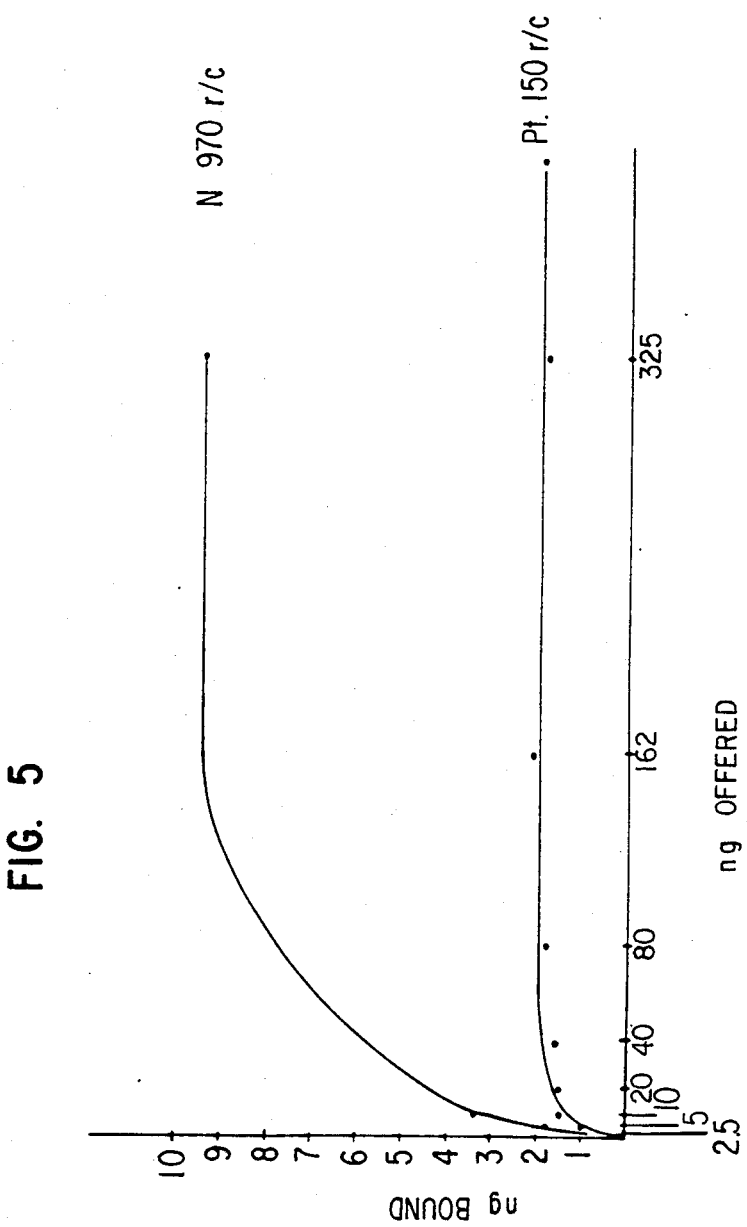
FIG. 5 is a graph illustrating the specific binding of $^{125}$I-labelled Fab' portion of Mab 543 to CR1 on erythrocytes (red blood cells) of normal patients (N), used as a control, and erythrocytes of patients having a selective deficiency of CR3 receptor (G). The binding curves represent $2.812 \times 10^9$ G erythrocytes/ml and $2.175 \times 10^9$ N erythrocytes/ml, respectively, each incubated with a buffer of Hank's Balanced Salt Solution diluted 1:2 in water and containing 0.2 percent ovalbumin, 2.5 percent dextrose and 0.01 M EDTA [DAHOSE] prior to CR1 quantitation with $^{125}$I-labelled Fab' portion of Mab 543.

FIG. 5 shows the results for $2.812 \times 10^9$ red blood cells/ml of patients having a selective deficiency of CR3 receptors in DAHOSE buffer and for $2.175 \times 10^9$ red blood cells/ml of normal patients in DAHOSE buffer. By the above assay method, about 970 CR1/cell were found for the normal patients and about 150 CR1/cell were found for the patients with the CR3 receptor deficiency, as shown in FIG. 5. Thus, these patients also showed reduced levels of erythrocyte CR1.

Figure 6:
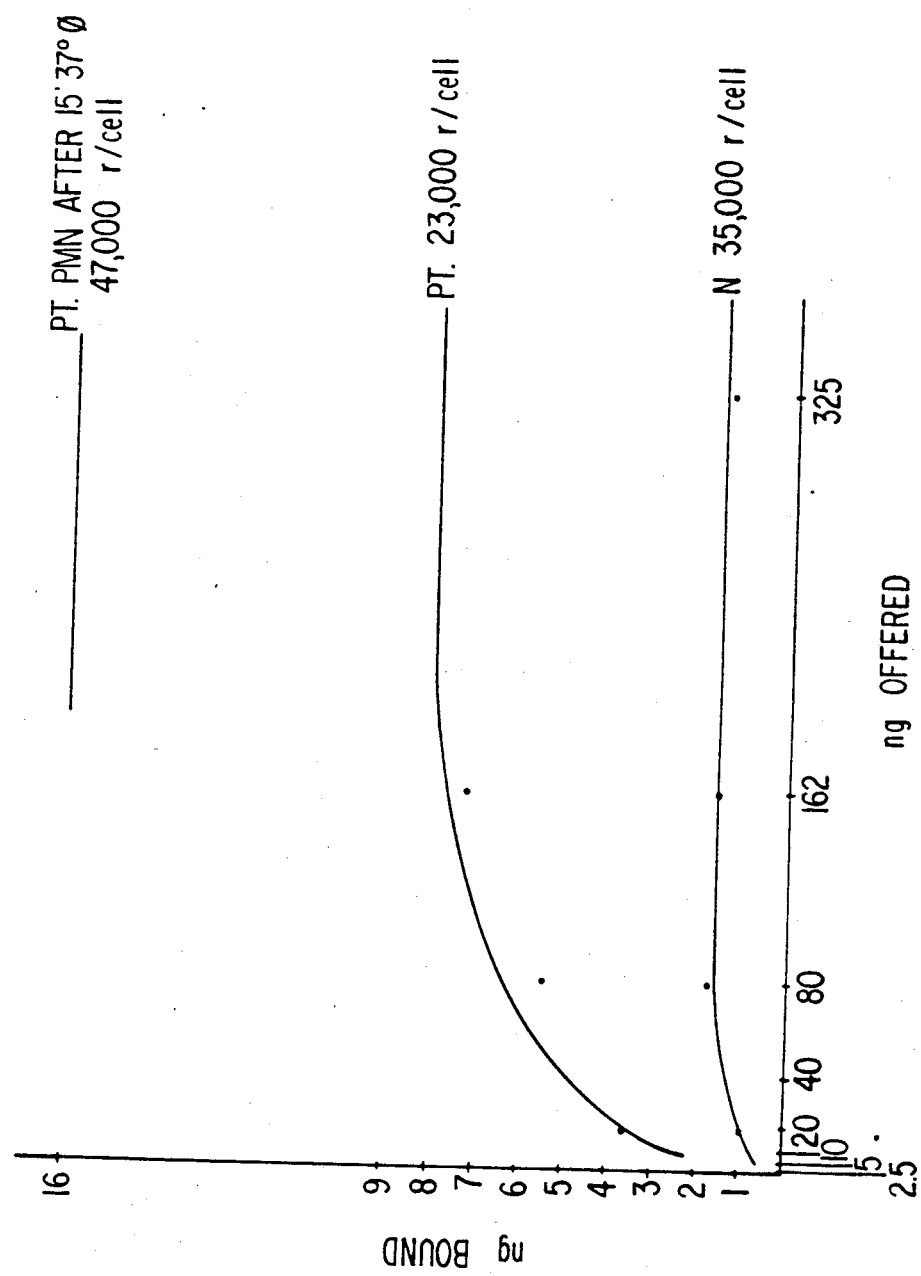
FIG. 6 is a graph illustrating the specific binding of $^{125}$I-labelled Fab' portion of Mab 543 to CR1 on polymorphonuclear leukocytes (PMN) of normal patients (N), used as a control, and PMN of patients having a selective deficiency of CR3 receptor (G). The binding curves represent $7.5 \times 10^7$ G PMN/ml and $1.13 \times 10^7$ N PMN/ml, respectively, each incubated with the buffer solution described above for FIG. 5 prior to CR1 quantitation with $^{125}$I-labelled Fab' portion of Mab 543. The uppermost plot of FIG. 6 shows specific binding of the $^{125}$I-labelled Fab' portion of Mab 543 to the G PMN after the PMN were warmed for 15 minutes at 37° C. before staining the the $^{125}$I-Fab', as described in Fearon et al., *J. Immunol.*, 130, 370 (1983).

FIG. 6 illustrates the results using the above assay method for screenings of $7.5 \times 10^7$ PMN/ml of patients having a selective deficiency of CR3 receptors in DAHOSE buffer and for $1.13 \times 10^7$ PMN/ml of normal individuals in DAHOSE buffer. After preincubation at 4° C., about 23,500 CR1/cell were found for normal individuals and about 35,200 CR1/cell were found for patients having the CR3 receptor deficiency.

The results in FIG. 6 also demonstrate that when the PMN cells of the patients with the CR3 receptor deficiency were warmed, the number of CR1/cell found increased. After warming for 15 minutes at 37° C., about 47,000 CR1/cell were found.

The above assay method was also utilized to determine CR1 density in patients with Hansen's disease (leprosy).

Figure 7:
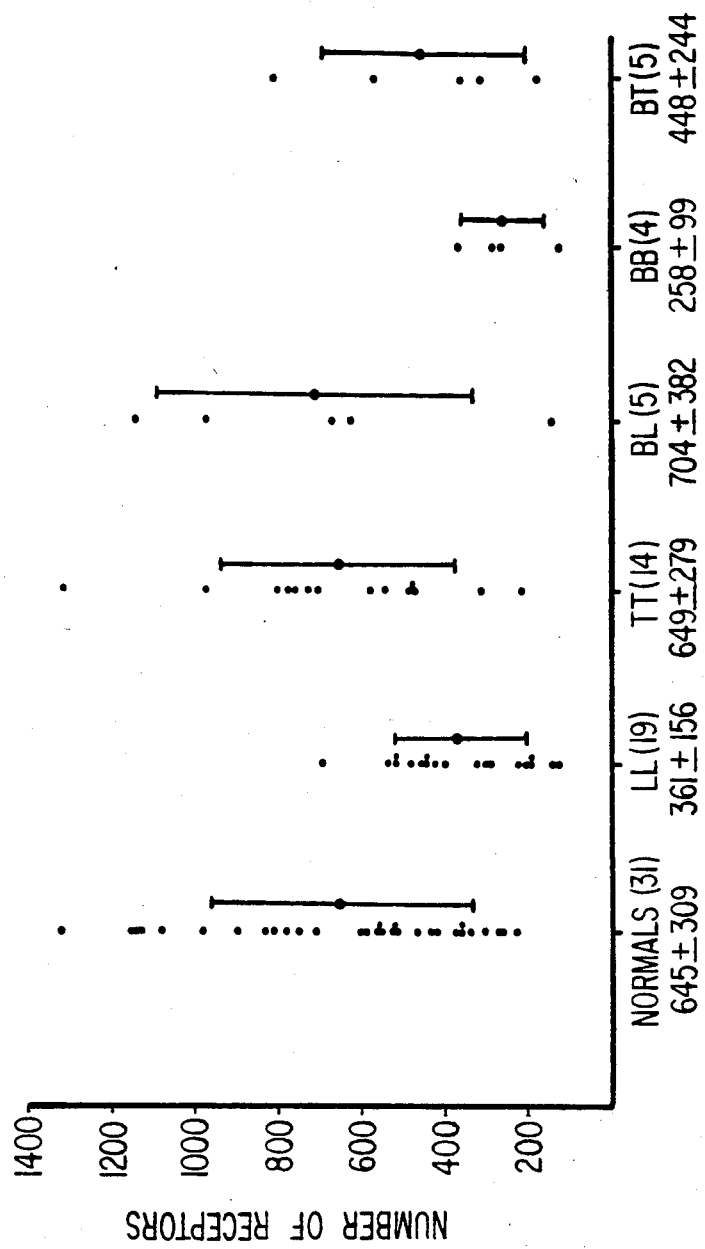
FIG. 7 is a graph illustrating the number of CR1 found on erythrocytes of normal patients, lepromatous (LL), tuberculoid (TT), borderline lepromatous (BL), borderline (unclassifiable) (BB) and borderline tuberculoid (BT) patients. An analysis of the data by Student's t-test, Snedecor et al., "Statistical Methods", 6th ed., Iowa State University Press, p. 1 (1967), showed a significant difference ($p$ 0.001) between LL and TT patients as well as between LL patients and normal patients. Bars represent means+SD (standard deviation) for each patient group.

Thirty-one normal individuals were found to have a mean of 645 CR1 per erythrocyte with a SD of $\pm$309. Nineteen patients diagnosed as having lepromatous leprosy had a mean of 361 CR1 molecules per erythrocyte with a SD of $\pm$156, while fourteen tuberculoid patients showed a mean of 649 CR1 per erythrocyte with a SD, of $\pm$279. These results demonstrate a significant difference when comparing the lepromatous patients with either the tuberculoid or normals (p $<$0.001), as shown in FIG. 7. Five borderline lepromatous, four borderline and five borderline tuberculoid patients were also screened.

The presence of erythema nodosum leprosum was not associated with a significant difference in CR1 expression levels. At the time of the screenings only three patients were without treatment. When assayed after treatment, the number of CR1 per erythrocyte did not change. However, since both the lepromatous pole and the tuberculoid received similar antibacterial treatment (Dapsone, Jacobus Pharmaceutical Co., Inc., Princeton, NJ; Rifampin, Merrel Dow Pharmaceuticals Inc., Cincinnati, OH), it was unlikely that therapy had any influence on the expression of CR1. CR1 levels on erythrocyte surface of normal individuals as well as patients tested at various times throughout six months showed no significant variation.

The above results demonstrate that the monoclonal antibody combining site of the present invention, that is produced by fusion of a myeloma cell line and lymphocytes that produce antibodies that react (1) with isolated human C3b receptor (CR1) and (2) with C3b receptor-bearing cells, binds with CR1 and with CR1-bearing cells and tissues, such as erythrocytes, polymorphonuclear lymphocytes, monocytes, B lymphocytes, dendritic reticulum and B cells in germinal centers.

The hybridoma used in producing a monoclonal antibody combining site-containing molecule of the present invention (Mab 543) was deposited on July 31, 1984 in the American Type Culture Collection of Rockville, MD and bears the designation ATCC, HB 8592.

In order to demonstrate that Mab 543 recognizes an epitope different from the C3b ligand binding site, and thus is able to measure the total number of C3b receptors on cell surfaces, regardless of occupancy by the ligand, a further screening was performed.

Fifty microliters of human erythrocytes ($2.5 \times 10^9$/ml in DGVB), were added to 50 microliters of increasing dilutions of $^{125}$I-C3b dimers in DGVB ranging from 2 to 150 micrograms/ml and assayed as described above. Nonspecific binding was determined by presaturating the erythrocytes with anti-CR1 polyclonal IgG, raised in rabbits against purified CR1. The resulting binding curve indicated saturable binding of the $^{125}$I-C3b dimers to the erythrocytes ($8 \times 10^{-6}$ nanograms (ng) per cell) with an affinity ($K_a$) of $2.9 \times 10^7$ M$^{-1}$.

Fifty microliters of human erythrocytes at the same concentration as above were incubated with 50 microliters of DGVB or 50 microliters of C3b dimers at a concentration of 120 micrograms/ml in DGVB. After 45 minutes on ice, the erythrocytes were assayed by the method described above for the presence of CR1. As shown in FIG. 1, no significant difference was observed between the resulting binding curve of erythrocytes that were preincubated with C3b dimers or in buffer, thereby demonstrating that the presence of C3b ligand bound to the receptor did not impair the binding of the $^{125}$I-labelled Fab' portion of Mab 543 to a different site.

B. Diagnostic Methods and Systems

The above results also demonstrate that the diagnostic method of the present invention that utilizes the monoclonal antibody combining site-containing molecule of the present invention is useful for assaying for the presence of C3b receptor on human blood cells and tissue cells.

Several in vivo methods are also available for locating C3b receptor (CR1) using an imaging technique. In such methods, a monoclonal antibody combining site of the present invention is labeled with an indicator labelling means or "indicating group" or a "label". The indicating group or label is utilized in conjunction with the monoclonal antibody combining site-containing molecule as a means for determining that CR1 has bound to the antibody. When a monoclonal antibody of this invention is utilized for the in vivo imaging of CR1, as discussed below, it is preferred that the idiotype-containing polypeptide portions such as Fab, F(ab')$_2$ and Fab' portions be used rather than whole, intact antibodies. The reason for this preference stems principally from the fact that the presence of Fc or Fc' antibody portions from an animal species different from the animal whose CR1 is to be imaged can lead to subsequent immunological complications.

The terms "indicator labelling means", "indicating group" or "label" are used herein to include single atoms and molecules that are linked to the antibody combining site or used separately, and whether those atoms or molecules are used alone or in conjunction with additional reagents. Such indicating groups or labels are themselves well-known in immunochemistry and constitute a part of this invention only insofar as they are utilized with otherwise novel antibody combining sites, methods and/or systems.

The indicator labelling means can be a fluorescent labelling agent that chemically binds to antibodies or antigens without denaturing them to form a fluorochrome (dye) that is a useful immunofluorescent tracer. Suitable fluorescent labelling agents are fluorochromes such as fluorescein isocyanate (FIC), fluorescein isothiocyanate (FITC), dimethylamino-naphthalene S-sulphonyl chloride (DANSC), tetramethylrhodamine isothiocyanate (TRITC), lissamine thodamine B200 -sulphonyl chloride (RB 200 SC) and the like. A description of immunofluorescence analysis techniques is found in Marchalonis et al., "Immunofluorescence Analysis", 189-231, that is incorporated herein by reference.

The indicator labelling means can be linked directly to an antibody combining site-containing molecule of this invention, to a useful antigen, or may comprise a separate molecule. It is particularly preferred that the indicator means be a separate molecule such as antibodies that bind to an antibody combining site-containing molecule of this invention. *Staphylococcus aureus* protein A, sometimes referred to herein as protein A, may also be used as a separate molecule indicator or labelling means where an intact or substantially intact antibody combining site of this invention is utilized. In such uses, the protein A itself contains a label such as a radioactive element or a fluorochrome dye, as is discussed hereinafter.

The indicating group may also be a biologically active enzyme, such as horseradish peroxidase (HRP) or glucose oxidase, or the like. Where the principal indicating group is an enzyme such as HRP or glucose oxidase, additional reagents are required to visualize the fact that an antibody-ligand complex has formed. Such additional reagents for HRP include hydrogen peroxide and an oxidation dye precursor such as diaminobenzidine. An additional reagent useful with glucose oxidase is 2,2'azino-di-(3-ethylbenzthiazoline-6-sulfonic acid) (ABTS).

Radioactive elements provide another class of label, and are used herein as exemplary of useful labels. An exemplary radiolabelling agent that may be utilized in the invention is a radioactive element that produces gamma ray emissions. Elements that themselves emit gamma rays such as $^{125}$I represent one class of gamma ray emission-producing radioactive element indicating groups. Another class of useful indicating groups are those elements such as $^{11}$C, $^{18}$F, $^{15}$O and $^{13}$N that themselves emit positrons. The positrons so emitted produce gamma rays upon encounters with electrons present in the medium.

A radioactive monoclonal antibody combining site-containing molecule can be made by culturing the hybridoma cells in a medium containing radioactive amino acids, as is well known, as well as by isolating the monoclonal antibody combining site-containing molecule and then labelling the monoclonal antibody combining site-containing molecule with one of the above radioactive elements as described in U.S. Pat. No. 4,381,292.

The radiolabelled antibody combining site-containing molecule such as Mab 543 or the idiotype-containing polypeptide portion thereof is then introduced as by injection into the blood stream of an animal. The labelled antibody combining site-containing molecule forms a complex with the CR1 on the blood or tissue cell surfaces, and after a suitable, predetermined time, such as about 18 to about 24 hours to permit clearance of unbound labelled antibody combining site from the body, the animal or a portion is scanned.

The animal is scanned with a gamma ray emission counting machine such as the axial tomographic scanner commercially available under the designation CT (80-800 CT/T) from General Electric Company (Milwaukee, WI), or with a positron emission transaxial tomography scanner such as that designated Pett VI located at Brookhaven National Laboratory.

In another embodiment, Mab 543 is labeled with an indicating group containing an element that is active in nuclear magnetic resonance (NMR) spectroscopy; i.e., an NMR-active element. Many such elements are commercially available in useful form and are exemplified by $^{13}$C, $^{15}$N, $^{19}$F and the like.

It is particularly preferred to utilize an indicating group containing the NMR-active $^{19}$F atom, or a plurality of such atoms inasmuch as (i) atom, or a plurality of such atoms inasmuch as (i) substantially all of naturally abundant fluorine atoms are the $^{19}$F isotope and thus substantially all fluorine-containing compounds are NMR-active; (ii) many chemically active polyfluorinated compounds such as trifluoroacetic anhydride are commercially available at relatively low cost, and (iii) many fluorinated compounds have been found medically acceptable for use in humans such as the perfluorinated polyethers utilized to carry oxygen as hemoglobin replacements.

Another particular advantage of the use of fluorine-containing NMR-active indicating groups is that the body contains very little fluorine under normal conditions. Consequently, by using an NMR-active element that is otherwise substantially absent from the animal, background signals due to bodily fluorine atoms are substantially absent. Thus, the principal signals observed are due to the labelled antibody-CR1 complex.

In this embodiment, an antibody combining site-containing molecule such as Mab 543 is preferably labelled with a fluorine-containing material such as trifluoroacetic anhydride or hexafluoroethanol to form a fluorinated amide or ester derivative, respectively. Thereafter the fluorinated antibody combining site-containing molecule is introduced as by injection into the bloodstream of the animal. After a predetermined amount of incubation time for the labelled antibody to complex with CR1 on the cell surfaces, a so-called "whole body" NMR determination is carried out using an apparatus such as one of those described by Pykett, *Scientific American*, 246, 78–88 (1982) to locate and form an image of the CR1.

Thus, the above methods of locating and quantitating CR1 in vivo in an animal include the steps of:

(a) providing a composition containing an antibody combining site-containing molecule of the present invention wherein the antibody combining site-containing molecule such as Mab 543 is bonded to an indicating group. Typical compositions include about 1 to about 100 milligrams of the labelled antibody combining site-containing molecule in an aqueous, diluent medium such as that provided by water alone, an aqueous saline, phosphate-buffered saline or other aqueous buffer solution. The amount of antibody combining site-containing molecule utilized depends, inter alia, upon the animal and the class of antibody combining site-containing molecule where an intact antibody is used. The useful indicating groups include gamma ray emission-producing elements, NMR-active elements and the like.

(b) The composition so provided is introduced into the blood stream of an animal, as by injection.

(c) The animal so injected is maintained for a predetermined period of time sufficient for the indicating group-bonded antibody combining site-containing molecule to form an immunecomplex on the surface of the blood or tissue cells, and preferably for non-bound, labelled antibody combining site-containing molecule to clear from the animal's body.

(d) The animal is then scanned with a means for detecting the location of the complexed indicating group. Typical detecting means include usually used gamma ray emission detectors, those machines used in positron emission tomography and so-called "whole body" NMR spectrometers that may in practice only scan a portion of the body at any time.

Several in vitro methods are available for detecting the presence of CR1 in a sample to be assayed.

In one embodiment of the invention, a solid assay method for detecting the presence and quantity of CR1 in a sample, that may be either (1) cells suspended in an aqueous medium such as PBS or (2) in a body fluid such plasma or serum, to be assayed is contemplated. This method comprises the steps of: (a) providing a solid matrix on which to assay a sample; (b) admixing an aliquot of a liquid sample (cell suspension, plasma, serum or the like) to be assayed with the solid matrix to form a solid-liquid phase admixture; (c) maintaining the admixture for a predetermined time (typically about 0.2 to about 2 hours) sufficient for the sample to affix to the matrix and form a solid phase support; (d) separating the solid and liquid phases; (e) admixing an antibody combining site-containing molecule of this invention with the separated solid phase to form a second solid-liquid phase admixture; (f) maintaining the second solid-liquid phase admixture for a predetermined time (typically about 0.2 to about 2 hours) sufficient for the antibody combining site-containing molecule to immunocomplex with CR1 present in the sample; (g) separating the solid and liquid phases; and (h) determining the presence and quantity of CR1 that immunocomplexed with the antibody combining site-containing molecule.

The presence of the CR1 that immunocomplexed with the antibody combining site-containing molecule may be determined in a number of ways. In one preferred embodiment, that determination is made by the steps of (i) admixing a liquid solution containing an indicator labelling means (such as described hereinabove) with the solid-liquid phase admixture, the indicator labelling means providing a means of detecting the presence of the antibody combining site-containing molecule that reacted with CR1; (ii) maintaining the admixture for a predetermined time (typically about 0.2 to about 2 hours) sufficient for the indicator labelling means to immunocomplex with the antibody combining site-containing molecule; (iii) separating the solid and liquid phases of the third solid-liquid phase admixture; and (iv) determining the presence of antibody combining site-containing molecule that immunocomplexed with CR1.

In yet another method, the presence of CR1, that immunoreacted with the antibody combining site-containing molecule of the invention may be determined with the indicator labelling means being linked directly to the antibody combining site-containing molecule. The presence of CR1 is determined by the label.

For example, the proteins present in a sample to be assayed may be radiolabelled with $^{125}$Iodine following one of the procedures described hereinafter. After separation of the solid and liquid phases of step (g), hereinbefore, the radiolabelled, but unbound, proteins are removed from the admixture thereby leaving radiolabelled, immunocomplexed CR1 on the solid support. The presence of that bound, radiolabelled CR1 can then be determined using a gamma counter. A similar result can be obtained using a reactive fluorescent molecule as the indicator labelling means such as fluoroscein isocyante to react with the components of the assayed sample in place of the radioactive element.

In another embodiment of the invention, an assay method for detecting the presence and quantity of CR1 in a tissue sample to be assayed is contemplated. The method comprises the steps of: (a) providing a tissue sample to be assayed; (b) contacting the sample with the antibody combining site-containing molecule of the invention that binds to CR1 for a predetermined time (typically about 0.2 to about 2 hours) sufficient for the antibody combining site-containing molecule to react with CR1 present in the sample to form an immunocomplex: (c) contacting the immunocomplex with an indicator labelling means for a predetermined time (typically about 0.2 to about 2 hours) sufficient for the indicator labelling means to immunocomplex with the antibody combining site-containing molecule, the indicator labelling means providing a means of determining the presence of antibody combining site-containing molecule that reacted with CR1; and (d) determining the presence of antibody combining site that reacted with CR1.

The presence of CR1 in a tissue sample may alternatively be determined by (i) combining the immunocomplex of step (b) above, after unreacted antibody combining site-containing molecule is removed, with a binding agent such as a second antibody or protein A that binds to the molecule containing the antibody combining site-containing molecule of the invention for a predetermined time (typically about 30 minutes) sufficient for the binding agent, e.g. second antibody, to react with the antibody combining site-containing molecule of the invention to form a second complex: (ii) contacting the second complex with a liquid solution containing an indicator labelling means that provides a means of detecting the presence of antibody combining site of the invention that reacted with CR1; and (iii) determining the presence of binding agent that reacted with the antibody combining site-containing molecule CR1 complex. A preferred binding agent is a goat anti-mouse IgG (heavy and light chain specific) available from Tago, Burlingame, CA.

The monoclonal antibody combining site-containing molecule of the invention may also be utilized in a diagnostic system for assaying for the presence and quantity of CR1 in blood and tissue cells. The system includes in at least one container that contains as an active ingredient, an effective amount of the monoclonal antibody combining site-containing molecule of the invention in dry, solution or dispersion form. The system may also contain an indicating means, such as those described above, which when introduced into a sample, binds selectively with the monoclonal antibody combining site.

The diagnostic system may also include a solid matrix that may be 96 well microtiter plates sold under the designation Falcon Microtest III Flexible Assay Plates (Falcon Plastics, Oxnard, CA) or a microtiter strip or plate containing twelve wells in a row, such as those strips and plates sold under the designations Immulon I and II, respectively, (Dynatech,, Alexandria, VA). The microtiter strip or plate is made of a clear plastic material, preferably polyvinyl chloride or polystyrene. Alternative solid matrices for use in the diagnostic system and method of this invention include polystyrene beads, about 1 micron to about 5 millimeters in diameter, available from Abbott Laboratories, North Chicago, IL; polystyrene tubes, sticks or paddles of any convenient size; nitrocellulose sheets, paddles or sticks; polystyrene latex whose polystyrene particles are of a size of about 1 micron and can be centrifugally separated from the latex; and dibutylphthalate and/or dioctylphthalate in polypropylene tubes.

The solid matrix may also be made of a variety of materials such as cross-linked dextran, e.g., Sephadex G-25, -50, -100, -200 and the like available from Pharmacia Fine Chemicals of Piscataway, New Jersey, agarose and cross-linked agarose, e.g., Sepharose 6B, CL6B, 4B, CL46 and the like also available from Pharmacia Fine Chemicals.

The diagnostic system may further include a standard against which to compare the assay results and various buffers in dry or liquid form for, inter alia, washing the wells, diluting the sample or diluting the labelled reagent.

III. MATERIALS AND METHODS - REGULATION of C3b,Bb ON NORMAL HUMAN ERYTHROCYTES

A. Purified Components

C3, cobra venom factor, nephritic factor and factors B, D, H and I were prepared as described in Hammer et al., *J. Biol. Chem.*, 256, 3995 (1981); Ballow et al., *J. Immunol.*, 103, 944 (1969); Schreiber et al., *J. Exp. Med.*, 142, 760 (1975); Gotze et al., *J. Exp. Med.*, 134, 905 (1971); Lesavre et al., *J. Immunol.*, 123, 529 (1979); and, Pangburn et al., *J. Exp. Med.*, 146, 257 (1977), respectively. CR1 was purified from 20 units of packed human erythrocytes by using the method of Fearon, *Proc. Natl. Acad. Sci. (USA), supra,* as modified by Dobson et al., *J. Immunol.*, 126, 693 (1981). The preparation produced 1.4 mg of purified CR1, which migrated as a single electrophoretic species with a $M_r$ of 205,000 on polyacrylamide gels in the presence of sodium dodecyl sulfate (SDS) and reducing agent, e.g. dithiothreitol. DAF was purified as described in Nicholson-Weller et al., *J. Immunol., supra* with the following modifications. Stroma were solubilized with Nonidet P-40 (NP-40; polyoxyethylene (9) nonyl phenyl ether) (Sigma, St. Louis, MO) and applied to a column of Bio-Rex 70 (BioRad, Richmond, CA) as described for the purification of CR1, Fearon, *Proc. Natl. Acad. Sci. (USA), supra.* The unadsorbed fraction was used in place of the butanol extract and applied directly to a DEAE-Sephacel column (Pharmacia Fine Chemicals, Piscataway, NJ), Nicholson-Weller et al., *J. Immunol., supra.* The purification yielded a protein with a $M_r$ of 71,000 on polyacrylamide gels in the presence of SDS and reducing agent.

B. Buffers and Reagents

Buffers used were designated VBS (10 mM veronal/150 mM NaCl, pH 7.4), GVB (VBS containing 0.1 percent gelatin), and GVBE (GVB containing 10 mM EDTA). Pronase was purchased from Sigma (St. Louis, MO). C3 and factor B were iodinated by using IODO-GEN (Pierce, Rockford, IL), according to the manufacturer's directions. Specific activities were approximately 1 microCi/microgram.

C. Cells

Normal human erythrocytes were washed free of plasma proteins with VBS and incubated with Pronase (5 mg/ml) in the same buffer for 30 minutes at 37° C. Deposition of C3b on erythrocytes and zymosan was accomplished as described in Pangburn et al., *supra,* and Pangburn et al., *Proc. Natl. Acad. Sci. (USA),* 75, 2416 (1978). Cells bearing between 30,000 and 60,000 C3b molecules per cell determined by factor H binding, Pangburn et al., supra, were used.

D. Antisera

Rabbit antisera were raised by two injections of purified CR1 (50 micrograms) or DAF (10 micrograms emulsified in complete Freund's adjuvant (GIBCO, Grand Island, NY) and injected at multiple sites. The IgG fraction was purified by passing 10 ml of antiserum over a *Staphylococcas aureus* protein A-Sepharose column (Sigma, St. Louis, MO) at pH 7.4, and eluting the bound IgG at pH 2.3. Antisera were tested by reaction with purified CR1 in an enzyme-linked immunosorbent assay (ELISA) and by inhibition of CR1-mediated rosetting of C3b-coated erythrocytes designated EC3b, or of C3b-coated microspheres (Covalent Technology, Ann Arbor, MI) by human polymorphonuclear leukocytes.

E. Monoclonal Antibodies

Monoclonal antibody 543 was produced by immunization with human CR1 using a modification of the standard hybridoma technology of Kohler et al., *Nature*, 256, 495 (1975). Briefly, BALB/c mice were immunized by two intraperitoneal injections of 10 micrograms of purified isolated from human erthrocytes. Their splenocytes were removed and a suspension of the splenocytes was made. The splenocytes were then fused with the murine myeloma cell P3×63-Ag8.653 at a ratio of 6:1 in the presence of a cell fusion promoter (polyethylene glycol 2000) three days after the last injection to form hybridomas.

Hybridoma 543 was selected by growth in Dulbecco's Modified Eagle's Medium (DMEM) containing 10 percent heat-inactivated fetal calf serum (FCS), 4 mM 1-glutamine, 1 mM sodium pyruvate, 0.1 mM nonessential amino acids, 50 units/ml penicillin, 50 micrograms/ml streptomycin, 0.05 units/ml gentamicin, $5 \times 10^{-5}$ M 2-beta-mercaptoethanol, to form an SDMEM medium, and Hypoxanthine, Aminopterin and Thymidine; i.e., (HAT) medium (14 micrograms/ml H), 16.5 nanograms (ng)/ml (A) and 8 micrograms/ml (T), that will not support growth of the unfused myeloma cells, and was subcloned using limiting dilution and culturing in separate containers. The resulting supernatant in each container was evaluated for the presence of the isotype of the Mab 543 with the Litton Bionectics Kit (Litton Bionectics, Kenginston, MD) as described in the kit instructions. The desired hybridoma was selected and cloned and Mab 543 was recovered from the supernatant above the clones. The fusion, cloning and expansion of the hybridoma are described in greater detail hereinafter.

Alternatively, the monoclonal antibody of the present invention may be produced by introducing, as by injection, the hybridoma into the peritoneal cavity of a mammal such as a mouse. Preferably syngenic or semi-syngenic mammals such as mice are used, as in U.S. Pat. No. 4,361,549, whose illustrative teachings of which are incorporated herein by reference. The hybridoma introduction causes formation of antibody-producing hybridomas after a suitable period of growth, e.g. 1–2 weeks, and results in a high concentration of the antibody being produced that can be recovered from the bloodstream and peritoneal exudate (ascites) of the host mouse. Although the host mammals also have normal antibodies in their blood and ascites, the concentration of normal antibodies is only about five percent that of the monoclonal antibody concentration. The resulting monoclonal antibody is used without purification or can be recovered from the ascites or serum of the mammal using standard techniques such as affinity chromatography on protein A-Sepharose (Pharmacia Fine Chemicals, Piscataway, NJ), followed by elution from the immunosorbant using an acidic buffer such as glycine hydrochloride at a pH value of about 2.5.

Mab 543 binding ability was demonstrated by reaction with purified CR1 in an ELISA.

F. Fusion

The mouse, immunized with human CR1, was anesthetized with diethyl ether, its entire body swabbed with 70 percent ethanol and was then transferred to a sterile environment. Whole blood was obtained from the mouse by either cutting the axial artery under the fore paw or by retraorbital bleeding. The immune sera were then separated, heat inactivated and stored for study.

The mouse was later swabbed again with 40 percent ethanol, anesthetized, and an incision, through the skin only, was made at mid-belly. The skin was pulled away towards either end of the animal to expose the peritoneum. The spleen was removed and placed in a petri dish containing HBSS without calcium or magnesium ions ($Ca^{++}$ or $Mg^{++}$), and was washed by sequentially transferring it into three petri dishes containing fresh HBSS without calcium or magnesium ions. The excised tissue was maintained at room temperature for the entire procedure.

The spleen was then transferred into a small petri dish containing 1 ml of HBSS without calcium or magnesium ions. The spleen was opened at one end and the splenocytes forced out by pressing along the entire length of the spleen with shafts of two bent 18 gauge needles. Clumps of cells recovered were disaggregated with a Pasteur pipette and a suspension was sedimented in a 15 ml conical tube for five minutes. The remaining cells in suspension were washed three times; first in HBSS without $Ca^{++}$ or $Mg^{++}$, then in 50 percent HBSS without $Ca^{++}$ or $Mg^{++}$ and 50 percent DMEM high glucose with no additives, and finally in 100 percent DMEM high glucose with no additives.

The splenocytes were subsequently resuspended in 10 ml of DMEM high glucose with no additives. Cell number and viability were determined by trypan blue (Gibco Laboratories, Grand Island, NY) exclusion in a hemocytometer cell counter (American Hospital Supply, Evanston, IL).

Myeloma cells that had been precounted for total number and viability were washed three times and standardized to $1 \times 10^7$ cells/ml in DMEM high glucose with no additives to form a suspension.

The splenic and myeloma cell suspensions were then mixed together and pelletized in a 15 ml conical tube to equal a final ratio of 6:1 (murine splenic: murine myeloma). The supernatant was then completely removed and the pellet coated over the bottom apex of the tube by running the tube along a grated surface.

The following procedure was done at room temperature.

After the fusion pellet was dispursed, a 40 percent polyethylene glycol 2000 (PEG) mixture was made by pipetting 0.6 ml DMEM high glucose (no additives) into a 1 ml pipette and then pipetting 0.4 ml of dissolved PEG at 56° C. into the pipette to form a total volume of 1 ml. The resulting mixture was combined in a small tube and taken up again in the pipette. While rotating the tube, the PEG mixture was added to the pellet during a 30 second interval at a rate of 1.5 second/drop. The resulting PEG-cell mixture was then gently rotated for 30 seconds.

The PEG-cell mixture was subsequently diluted by adding 1 ml DMEM-10 percent FCS during a period of one minute with gentle rotation of the tube. This was then repeated during a second minute. Thereafter, 8 ml DMEM-10 percent FCS was added during each of the following two minutes for a total addition of 10 ml during a four minute period to form a fusion mixture.

The fusion mixture so prepared was centrifuged at 800 revolutions per minute (rpm) for 10 minutes, and the pellet gently was resuspended with a large bore pipette into 50 ml SDMEM-10 percent FCS solution thereby forming a final fusion suspension that was distributed in the amount of 50 microliters/well into flat-bottom microtiter plates having 96 wells, each containing 100 microliters/well murine peritoneal exudate cells at $2 \times 10^5$ cells/ml.

Myeloma cells in a density proportional to that of the myeloma cells used in the fusion were cultured with HAT-SDMEM-10 percent FCS in 24 well plates. These myeloma cells died within one week to create a control for an original HAT sensitive culture.

Twenty-four hours after the fusion had taken place, 50 microliters of SDMEM-10 percent FCS and four-fold concentrated, HAT. were added to each of the 96 wells per plate. At seven and eleven days after the fusion, one-half of the supernatant (100 microliters) from each well was replaced with fresh SDMEM-10 percent FCS and HAT. From a time period of fourteen days after the fusion, or when growth was visible in the wells, the hybridomas were fed every two days with SDMEM-10 percent FCS and HAT by replacing one-half of the culture supernatant.

G. Cloning

The preferred method for the preservation of an antigen-positive antibody-producing hybridoma is to clone the hybridoma directly out of its fusion plate. Such cloning prevents it from being overgrown by a nonproducer; i.e., if all the fusion products in the well were first expanded and then cloned.

The antibody-producing hybridoma was allowed to become at least 80 percent confluent in its fusion well. Fast growth was promoted by feeding the hybridoma as described above 1-2 days prior to cloning. The contents of the well were then gently resuspended using a Pasteur pipette or a 2 ml sterile plastic pipette with a sterile bulb attached by squeezing the bulb in and out. The total volume in the well was maintained at 200 microliters.

When the resulting suspension was fully mixed, 10 microliters were removed, and were diluted 1:2 with trypan blue dye. Cell density and viability were then determined using a hemocytometer.

Limiting dilutions for cloning were then made as follows wherein the number of cells per well were calculated averaged values: (a) 500 cells/ml (10 ml of medium containing 5000 cells); (b) 100 cells/ml (8 ml of medium and 2 ml at 500 cells/ml) (dilution A); and (c), 20 cells/ml (16 ml of medium and 4 ml at 100 cells/ml) (dilution B). These cloning dilutions were then introduced into two 96 well, flat-bottom plates containing $2 \times 10^4$ PECS/well as follows: (a) 100 microliters/well at 500 cells/ml were added to the top row of each plate (12 wells/plate); (b) 100 microliters/well at 100 cells/ml were added to the second row of each plate (12 wells/plate); and (c) 100 microliters/well at 20 cells/ml were added to all of the remaining wells on each plate (72 wells/plate).

This cloning procedure yielded an average of about 50 cells/well along the top row, about 10 cells/well along the second row and about 2 cells/well in the remaining 72 wells of each plate.

The remaining undiluted cells from the original fusion well were then transferred into one well of a 24 well plate and diluted to a final volume of 1 ml to form a suspension. The suspension was subsequently used to wash the original well and 200 microliters of the suspension were added to the fusion well. When the cells of the 24 well plate became confluent, they were either frozen for retention or expanded.

Clones typically appeared in the wells after approximately seven days. When a noticeable color change and a clonal pattern of growth were observed, screening and a feeding schedule of alternate days or every third day were initiated. When a positive clone was identified, the cloning procedure was repeated until a single clone was obtained.

H. Expansion

When a desirable hybridoma was sufficiently cloned, it was expanded for the initial purpose of freezing. For the expansion procedure, the hybridoma was resuspended in its clonal well with a Pasteur pipette without creating turbulence in the well. The resulting suspension was then transferred into one well of a 24 well plate containing 1 ml of medium (SDMEM) and a peritoneal exudate cell (PEC) feeder layer of $1 \times 10^5$ PECs/well.

The original well was then washed with 0.2 ml of fresh medium which was added to the well. Finally, 0.2 ml of the cell suspension in the 24 well plate was added back to the clonal well. After one day or when a slight color change was observed, the cells were fed with 1 ml of fresh medium.

When the cells were approximately 80 percent confluent, they were split 1:2 as follows: (a) the cells were resuspended with a 5 ml pipette; (b) 1 ml of cell suspension was transferred into an adjacent well; and (c) both the original well and the new well were given 1 ml of fresh medium.

When two wells of the 24 well plate were approximately 80 percent confluent, the 1:2 split was repeated for each well to create a total of four wells. When the four wells were then 80 percent confluent, each well was split 1:4 by the addition of 0.5 ml of cell suspension to 1.5 ml of medium.

Each split required approximately 2-3 days to become confluent. When the entire plate became confluent, each well was resuspended, combined, spun and frozen to yield approximately 2-3 vials, each containing about $5 \times 10^6$ cells.

IV. MATERIALS AND METHODS - BINDING OF Mab 543 TO C3b RECEPTOR BEARING CELLS

A. Cells

Ten milliliters of venous blood were drawn from human donors in 0.02M ethylenediamine tetraacetate (Fisher Scientific, Fairlawn, NJ) filtered over glass wool and washed three times in phosphate buffered saline (PBS), removing any remaining buffy coat after each wash. The erythrocytes were then resuspended at a concentration of $2.5 \times 10^9$/ml in veronal buffered half-physiological saline (0.075 M NaCl) (DGVB) containing 2.5 percent dextrose (Mallinkrodt, Paris, KY) and 0.5 percent gelatin (J. T. Baker, Phillipsburg, NJ).

Monocytes were prepared by the procedure described in Sanderson et al., *J. Immunol.*, 118, 1409 (1977). Briefly, ten milliliters of heparinized blood (10 units/ml of sodium heparin) were drawn from adult human donors. The blood was diluted three-fold in 0.9 percent NaCl and layered over a Ficoll-Hypaque (FH) gradient in 40 ml test tubes. The FH was prepared to have a specific gravity of 1.078.

After centrifugation at $500 \times g$ for 40 minutes, the monocytes, along with a varying number of platelets, were concentrated in a thin layer between the FH and the saline-diluted plasma. The cells at the interface were removed with a Pasteur pipette and separated from the accompanying FH, plasma, and saline mixture by spinning a 750×g for 10 minutes. They were then washed twice in Ca++, Mg++ free HBSS by spinning at 200×g for 15 minutes, and the resulting pellet was resuspended in 5 ml of HBSS to be ready for loading into a counterflow centrifuge.

A Beckman J21B centrifuge (Beckman Instruments Inc., Palo Alto, CA) equipped with an elutriator rotor and a specially designed separation chamber, Sanderson et al., *Anal. Biochem.*, 71, 615 (1976), was used for the final fractionation of lymphocytes and monocytes. For monocyte isolation, a centrifuge speed of 2500 rpm, corresponding to 625×g at the downstream end of the separation chamber was used. The most concentrated monocyte fraction was eluted by using a flow rate of 28 ml of the elution of medium per minute. The elution medium was HBSS, Ca++ and Mg++ free, containing 5 mg/ml of human serum albumin.

Polymorphonuclear leukocytes were prepared as described in English et al., *J. Immunol. Methods*, 5, 219 (1974). Briefly, thirty milliliters of blood was mixed with 0.3 ml of heparin (1000 units/ml) or 0.3 ml of 0.2M EDTA, pH 7.2. The blood was then diluted with 30 ml of 0.9 percent NaCl and 15 ml of the diluted blood was layered over a Ficoll-Hypaque (FH) gradient in 50 ml centrifuge tubes. The lower separating layer contained 12 ml of FH made up from 16.5 ml of 50 percent Hypaque in water and 33.0 ml of 9 percent Ficoll in water. The upper separating layer contained 12 ml made up from 9.8 ml of 50 percent Hypaque, 4.7 ml of water, and 35.0 ml of 9 percent Ficoll in water.

After centrifugation at 800×g for 20 minutes at 25° C., the cells at the interface between the FH separation layers were removed and washed once with cold 0.85 percent NaCl in 250 ml bottles. One bottle was used per 15 ml of starting blood. The cells were then spun for 10 minutes at 200×g. The resulting cell pellet then had 20 ml of cold 5mM Tris, pH 8.0, added to it and was incubated for one minute prior to the rapid addition of 20 ml of 1.7 percent NaCl. The cells were then pelleted and resuspended in HBSS-0.1 percent ovalbumin. The yield was $1.47 \times 10^8$ cells.

B. Tissue Sections

The tissue sections were prepared by the procedure described in Fox et al., *J. Immunol.*, 132, 2883 (1984). Briefly, the tissue sections were prepared by Ficoll-Hypaque centrifugation. Suspensions of tissues were obtained by overnight digestion with collagenase (Calbiochem, San Diego, CA) at 37° C., followed by Ficoll-Hypaque centrifugation. Tissue sections may be frozen at −70° C. in 10 percent dimethyl sulfoxide and 20 percent fetal calf serum until thawing immediately before use.

C. Purified CR1 and Monoclonal Antibodies

CR1 was purified to homogeneity according to known methods, as described in Fearon, *Proc. Natl. Acad. Sci. (USA)*, 76, 5867 (1979); Dobson et al., *J. Immunol.*, 126, 693 (1981). Murine monoclonal antibody 543 was produced by using a modification, Tamerius et al., *J. Immunol.*, 128, 512 (1982), of the method of Kohler et al., *Nature*, 256, 495 (1975). Mice were immunized by two intraperitoneal injections of 10 micrograms of CR1. Spleen cells were fused with the murine myeloma line P3×63-Ag8.653 at a ratio of 6:1. The resulting antibodies were obtained as described in Section III hereinbefore and were tested by reaction with purified CR1 in an enzyme-linked immunosorbent assay. Clone 543 was shown to be of class IgG₁ and was used for further assays.

The IgG fraction was purified by passing ascites fluid, obtained as described in Section III hereinbefore, over a protein A-agarose column (EY, San Mateo, CA), equilibrated with 0.1 M phosphate buffer, pH 8, and the bound IgG was eluted with 0.1 M acetic acid, pH 3. Fab' fragments were obtained by digesting the IgG for 18 hours at 37° C. in the presence of 0.02M Cys-HCl (Sigma, St. Louis, MO) as reducing agent with 2 percent w/w pepsin at pH 4.0 (Sigma, St. Louis, MO). 0.025M Iodoacetamide was then added and the fragments were purified by HDLC (Waters, Millford, MA) gel filtration on a 7.5×600 millimeter TSK-250 column (BioRad, Richmond, CA).

D. Radiolabelling of 543 Fab' and C3b Dimers

Fab' fragments of Mab 543 and C3b dimers, Melamed et al., *J. Immunol.*, 128, 2313 (1982), were labeled using IODO-GEN coated tubes (Pierce, Rockford, IL) to a specific activity of 1 milliCurie/microgram according to the iodogen iodination procedure of Fraker et al., *Biochem. Biophys. Res. Commun.*, 80, 849 (1978). Free and protein bound $^{125}$I were separated by centrifugation through tubes of Bio-gel P6 (BioRad, Richmond, CA).

The foregoing is intended as illustrative of the present invention but not limiting. Numerous variations and modifications may be effected without departing from the true spirit and scope of the invention.

What is claimed is:

1. A solid phase assay method for detecting the presence of human C3b receptor in a sample to be assayed comprising the steps of:
    (a) providing a solid matrix on which to assay a sample;
    (b) admixing an aliquot of a liquid sample to be assayed with said solid matrix to form a solid-liquid phase admixture;
    (c) maintaining said admixture for a predetermined time sufficient for said sample to affix to said solid matrix and form a solid phase support;
    (d) separating the solid and liquid phases;
    (e) admixing a murine mococlonal antibody combining site-containing molecule with the separated solid phase to form a second solid-liquid phase admixture, said antibody combining site-containing molecule being produced by hybridoma ATCC HB 8592, the presence of C3b ligands bound to C3b receptors not impairing the binding of the Fab' portions of said antibody combining site-containing molecule to said C3b receptors;
    (f) maintaining said second solid-liquid phase admixture for a predetermined time sufficient for said antibody combining site-containing molecule to immunocomplex with C3b receptor present in said sample;
    (g) separating the solid and liquid phases; and
    (h) determining the presence of C3b receptor that immunocomplexed with said antibody combining site-containing molecule.

2. The method of claim 1 further comprising the additional steps of:
    (a) admixing a liquid solution containing an indicator labelling means with the solid phase obtained after step (g) to form a third solid-liquid phase admixture, said indicator labelling means providing a means of detecting the presence of said antibody combining site-containing molecule that immunocomplexed C3b receptor;

(b) maintaining said admixture for a predetermined time sufficient for said indicator labelling means to immunocomplex with said antibody combining site-containing molecule;

(c) separating the solid and liquid phases of said third solid-liquid phase admixture; and (d) determining the presence of said labelling means of said immunocomplex and thereby determining the presence of antibody combining site-containing molecule that immunocomplexed with C3b receptor.

3. The method of claim 2 wherein said sample contains human blood cells suspended in an aqueous medium.

4. The method of claim 2 wherein said sample contains human tissue cells.

5. An assay method for detecting the presence of human C3b receptor in a sample to be assayed comprising the steps of:

(a) providing a sample to be assayed;

(b) contacting said sample with a murine monoclonal antibody combining site-containing molecule produced by hybridoma ATCC HB 8592, the presence of C3b ligands bound to C3b receptors not impairing the binding of Fab' portions of said antibody combining site-containing molecule to said C3b receptors, said contact being for a predetermined time sufficient for said antibody combining site-containing molecule to specifically bind to an antigenic determinant of C3b receptor present in said sample to form an immunocomplex;

(c) contacting said immunocomplex with an indicator labelling means for a predetermined time sufficient for said indicator labeling means to immunocomplex with said antibody combining site-containing molecule, said indicator labelling means providing a means of determining the presence of antibody combining site-containing molecules that reacted with C3b receptor; and (d) determining the presence of antibody combining site-containing molecules that reacted with C3b receptor.

6. An assay method for detecting the presence of human C3b receptor in a sample to be assayed comprising the steps of:

(a) providing a sample to be assayed;

(b) contacting said sample with a first murine monoclonal antibody combining site-containing molecule produced by hybridoma ATCC HB 8592, the presence of C3b ligands bound to C3b receptors not impairing the binding of the Fab' portions of said antibody combining site-containing molecule to said C3b receptors, said contact being for a predetermined time sufficient for said first antibody combining site-containing molecule to specifically bind to an antigenic determinant of said C3b receptor present in said sample to form an immunocomplex;

(c) removing unreacted first antibody combining site-containing molecule from said sample;

(d) combining said immunocomplex with a second antibody combining site-containing molecule that binds to said first antibody combining site-containing molecule for a predetermined time sufficient for said second antibody combining site-containing molecule to react with said first antibody combining site-containing molecule to form a second immunocomplex;

(e) contacting said second immunocomplex with a liquid solution containing an indicator labelling means that provides a means of detecting the presence of said first antibody combining site-containing molecule that reacted with C3b receptor; and (f) determining the presence of second antibody combining site-containing molecule that reacted with said first antibody combining site-containing molecule immunocomplexed with C3b receptor.

7. The method of claim 6 wherein said sample contains human tissue cells.

8. The method of claim 6 wherein said sample contains human blood cells.

9. A murine, kappa, gamma$_1$ monoclonal antibody combining site-containing molecule produced by hybridoma ATCC HB 8592.

10. A diagnostic system for assaying for the presence of cellular C3b receptors and C3b receptor bearing cells, said system including in at least one container as an active ingredient an amount of a murine monoclonal antibody combining site-containing molecule produced by hybridoma ATCC HB 8592, said system including indicating means that, when introduced into a sample, binds selectively with said monoclonal antibody combining site-containing molecule, said antibody combining site-containing molecule and said indicating means being present in amounts sufficient to perform said assay.

11. The diagnostic system of claim 10 wherein said indicating means is bonded to said monoclonal antibody combining site-containing molecule.

12. The diagnostic system of claim 10 wherein said monoclonal antibody combining site-containing molecule is an Fab' fragment antibody portion individually bonded to said indicating means.

13. The diagnostic system of claim 10 wherein said monoclonal antibody combining site-containing molecule is an antibody individually bonded to said indicating means.

14. Hybridoma ATCC HB 8592.

15. A method of preparing a murine monoclonal antibody combining site-containing molecule which comprises culturing hybridoma ATCC HB 8592 in a suitable culture medium and recovering the antibody combining site-containing molecule.

16. The method of claim 15 which further comprises introducing said hybridoma is introduced into the peritoneal cabity of a host mammal, growing said hybridoma in said host mammal, and recovering the antibody combining site-containing molecule from the malignant ascites or serum of said mammal.

* * * * *

UNITED STATES PATENT AND TRADEMARK OFFICE
CERTIFICATE OF CORRECTION

PATENT NO. : 4,672,044

DATED : June 9, 1987

INVENTOR(S) : Robert D. Schreiber

It is certified that error appears in the above-identified patent and that said Letters Patent is hereby corrected as shown below:

Column 9, lines 41-60, Table 1 should appear as shown below:

Table I
AMINO ACID ANALYSIS

| Amino Acid | Residues/Molecule | | | |
|---|---|---|---|---|
| | Mab 543 (Whole) | | Mab 543 (Fab' portion) | |
| | Found | Rounded | Found | Rounded |
| Asx | 121.9 | 122 | 78.0 | 78 |
| Thr | 115.4 | 115 | 77.3 | 77 |
| Ser | 146.0 | 146 | 113.2 | 113 |
| Glx | 129.7 | 130 | 78.6 | 79 |
| Pro | 91.2 | 91 | 53.9 | 54 |
| Gly | 70.9 | 71 | 60.5 | 60 |
| Ala | 71.9 | 72 | 66.1 | 66 |
| Cys | 31.2 | 31 | ----- | ---- |
| Val | 103.0 | 103 | 71.0 | 71 |
| Met | 19.7 | 20 | 7.0 | 7 |
| Ile | 48.8 | 49 | 29.0 | 29 |
| Leu | 83.4 | 83 | 59.3 | 59 |
| Tyr | 58.5 | 58 | 47.9 | 48 |
| Phe | 56.2 | 56 | 32.3 | 32 |
| His | 31.8 | 32 | 18.7 | 19 |
| Lys | 83.3 | 83 | 45.0 | 45 |
| Arg | 42.2 | 42 | 32.0 | 32 |

UNITED STATES PATENT AND TRADEMARK OFFICE
CERTIFICATE OF CORRECTION

PATENT NO. : 4,672,044

DATED : June 9, 1987

INVENTOR(S) : Robert D. Schreiber

It is certified that error appears in the above-identified patent and that said Letters Patent is hereby corrected as shown below:

Column 9, line 62, delete "The" and insert --A molecules containing the --

Claim 16, line 3, delete "cabity" and insert --cavity--

Signed and Sealed this

Nineteenth Day of July, 1988

Attest:

DONALD J. QUIGG

Attesting Officer          Commissioner of Patents and Trademarks